(12) United States Patent
Haufe et al.

(10) Patent No.: US 9,883,882 B2
(45) Date of Patent: Feb. 6, 2018

(54) MINIMALLY INVASIVE METHODS FOR SPINAL FACET THERAPY TO ALLEVIATE PAIN AND ASSOCIATED SURGICAL TOOLS, KITS AND INSTRUCTIONAL MEDIA

(71) Applicant: Medovex Corp., Cumming, GA (US)

(72) Inventors: Scott M. W. Haufe, Niceville, FL (US); Adam L. Gullickson, Stillwater, MN (US); Robert D. Carter, Apple Valley, MN (US)

(73) Assignee: Medovex Corp., Cumming, GA (US)

( * ) Notice: Subject to any disclaimer, the term of this patent is extended or adjusted under 35 U.S.C. 154(b) by 809 days.

(21) Appl. No.: 14/257,490

(22) Filed: Apr. 21, 2014

(65) Prior Publication Data

US 2014/0324044 A1 Oct. 30, 2014

Related U.S. Application Data

(60) Provisional application No. 61/977,817, filed on Apr. 10, 2014, provisional application No. 61/815,416, filed on Apr. 24, 2013.

(51) Int. Cl.
*A61B 18/14* (2006.01)
*A61B 17/32* (2006.01)
(Continued)

(52) U.S. Cl.
CPC .... *A61B 17/32002* (2013.01); *A61B 17/3417* (2013.01); *A61B 17/3421* (2013.01);
(Continued)

(58) Field of Classification Search
CPC ...... A61B 18/1482; A61B 2018/00202; A61B 2018/00208; A61B 2018/00595; A61B 2018/00339; A61B 2018/0016; A61B 17/3417; A61B 17/3421; A61B 2017/320032; A61B 2017/3492;
(Continued)

(56) References Cited

U.S. PATENT DOCUMENTS 2,001,638 A 5/1935 Tornsjo
2,012,363 A 8/1935 Vogel
(Continued)

FOREIGN PATENT DOCUMENTS

CN 2064221 10/1990
CN 102641152 8/2012
(Continued)

OTHER PUBLICATIONS

International Search Report and Written Opinion for PCT Application No. PCT/US2015/040867, dated Apr. 1, 2016, 22 pages.
(Continued)

*Primary Examiner* — Thomas Giuliani
(74) *Attorney, Agent, or Firm* — Myers Bigel, P.A.

(57) ABSTRACT

Methods and surgical tools for treating back pain use a spinal facet debridement tool with cautery and denuding action and minimally invasive protocol that uses a low rotation speed and a power source configured with a cautery head with scraping elements that can denude and cauterize soft tissue associated with a synovial capsule of the spinal facet joint.

33 Claims, 25 Drawing Sheets

(51) Int. Cl.
*A61B 17/34* (2006.01)
*A61B 18/00* (2006.01)
*A61N 7/02* (2006.01)
*A61B 18/02* (2006.01)
*A61B 18/20* (2006.01)

(52) U.S. Cl.
CPC ........... *A61B 18/02* (2013.01); *A61B 18/1482* (2013.01); *A61B 18/20* (2013.01); *A61B 2017/320032* (2013.01); *A61B 2017/3407* (2013.01); *A61B 2017/347* (2013.01); *A61B 2017/3492* (2013.01); *A61B 2018/00339* (2013.01); *A61B 2018/00595* (2013.01); *A61N 7/022* (2013.01)

(58) Field of Classification Search
CPC ...... A61B 2017/3407; A61B 2017/347; A61B 18/04; A61B 18/08; A61B 18/082
USPC .......................................... 606/41, 49, 27–30
See application file for complete search history.

(56) References Cited

U.S. PATENT DOCUMENTS

| | | | |
|---|---|---|---|
| 4,002,169 A | 1/1977 | Cupler, II | |
| 4,314,568 A | 2/1982 | Loving | |
| 4,658,819 A | 4/1987 | Harris et al. | |
| 4,969,885 A | 11/1990 | Farin | |
| 4,983,179 A | 1/1991 | Sjostrom | |
| 4,991,578 A | 2/1991 | Cohen | |
| 5,312,332 A | 5/1994 | Bales et al. | |
| 5,364,395 A | 11/1994 | West, Jr. | |
| 5,545,195 A | 8/1996 | Lennox et al. | |
| 5,569,290 A | 10/1996 | McAfee | |
| 5,573,533 A | 11/1996 | Strul | |
| 5,584,843 A | 12/1996 | Wulfman et al. | |
| 5,618,296 A | 4/1997 | Sorensen et al. | |
| 5,633,578 A | 5/1997 | Eggers et al. | |
| 5,693,045 A | 12/1997 | Eggers | |
| 5,807,395 A | 9/1998 | Mulier et al. | |
| 5,819,734 A | 10/1998 | Deily et al. | |
| 5,849,023 A | 12/1998 | Mericle | |
| 5,855,576 A | 1/1999 | LeVeen et al. | |
| 5,865,810 A | 2/1999 | Perry et al. | |
| 5,904,681 A * | 5/1999 | West, Jr. ............... | A61B 18/148 604/22 |
| 5,941,876 A | 8/1999 | Nardella et al. | |
| 5,957,863 A | 9/1999 | Koblish et al. | |
| 6,007,533 A * | 12/1999 | Casscells ......... | A61B 17/32002 606/180 |
| 6,032,673 A | 3/2000 | Savage et al. | |
| 6,142,992 A | 11/2000 | Cheng et al. | |
| 6,214,001 B1 * | 4/2001 | Casscells ......... | A61B 17/32002 606/180 |
| 6,406,424 B1 | 6/2002 | Williamson, IV et al. | |
| 6,416,490 B1 | 7/2002 | Ellis et al. | |
| 6,454,764 B1 | 9/2002 | Fleenor et al. | |
| 6,579,281 B2 | 6/2003 | Palmer et al. | |
| 6,610,059 B1 * | 8/2003 | West, Jr. .......... | A61B 17/32002 606/41 |
| 6,663,628 B2 | 12/2003 | Peters | |
| 6,770,070 B1 | 8/2004 | Balbierz | |
| 6,827,725 B2 | 12/2004 | Batchelor et al. | |
| 6,979,332 B2 | 12/2005 | Adams | |
| 7,001,333 B2 | 2/2006 | Hamel et al. | |
| 7,052,494 B2 | 5/2006 | Goble et al. | |
| 7,150,747 B1 | 12/2006 | McDonald et al. | |
| 7,326,177 B2 | 2/2008 | Williamson, IV et al. | |
| 7,331,956 B2 | 2/2008 | Hovda et al. | |
| 7,361,174 B2 | 4/2008 | Bee et al. | |
| 7,674,263 B2 * | 3/2010 | Ryan .................... | A61B 18/148 606/180 |
| 7,736,361 B2 | 6/2010 | Palanker et al. | |
| 7,789,879 B2 | 9/2010 | Palanker et al. | |
| 7,942,874 B2 | 5/2011 | Eder et al. | |
| 8,012,153 B2 | 9/2011 | Woloszko et al. | |
| 8,043,286 B2 | 10/2011 | Palanker et al. | |
| 8,167,879 B2 | 5/2012 | Haufe | |
| 8,323,276 B2 | 12/2012 | Palanker et al. | |
| 8,343,189 B2 | 1/2013 | Assell et al. | |
| 8,394,129 B2 | 3/2013 | Lopez et al. | |
| 8,500,727 B2 | 8/2013 | Aramayo | |
| 2001/0000531 A1 | 4/2001 | Casscells et al. | |
| 2002/0165549 A1 | 11/2002 | Owusu-Akyaw et al. | |
| 2003/0153926 A1 | 10/2003 | Hamel et al. | |
| 2003/0195392 A1 | 10/2003 | Hamel et al. | |
| 2004/0030330 A1 | 2/2004 | Brassell et al. | |
| 2004/0078037 A1 | 4/2004 | Batchelor et al. | |
| 2005/0245923 A1 | 11/2005 | Christopherson et al. | |
| 2006/0058780 A1 | 3/2006 | Edwards et al. | |
| 2006/0095059 A1 | 5/2006 | Bleich et al. | |
| 2006/0178670 A1 | 8/2006 | Woloszko et al. | |
| 2007/0049920 A1 | 3/2007 | McClurken et al. | |
| 2007/0129719 A1 | 6/2007 | Kendale et al. | |
| 2007/0293724 A1 | 12/2007 | Saadat et al. | |
| 2008/0015565 A1 | 1/2008 | Davison | |
| 2008/0161670 A1 | 7/2008 | King et al. | |
| 2008/0163870 A1 | 7/2008 | Kusunoki et al. | |
| 2008/0188848 A1 | 8/2008 | Deutmeyer et al. | |
| 2008/0249553 A1 | 10/2008 | Gruber et al. | |
| 2009/0093683 A1 | 4/2009 | Richard et al. | |
| 2010/0010449 A1 | 1/2010 | Leibowitz et al. | |
| 2010/0145142 A1 | 6/2010 | Begemann et al. | |
| 2010/0191234 A1 * | 7/2010 | Haufe ................ | A61B 18/1477 606/37 |
| 2011/0087217 A1 | 4/2011 | Yates et al. | |
| 2012/0179070 A1 | 7/2012 | Pommer et al. | |
| 2013/0190809 A1 | 7/2013 | Vidlund et al. | |
| 2014/0100567 A1 | 4/2014 | Edwards et al. | |
| 2014/0100597 A1 | 4/2014 | Edwards | |
| 2016/0030106 A1 | 2/2016 | Carter et al. | |
| 2016/0213415 A1 | 7/2016 | Carter et al. | |

FOREIGN PATENT DOCUMENTS

| | | |
|---|---|---|
| CN | 202637105 | 1/2013 |
| WO | WO 97/33523 A1 | 9/1997 |
| WO | WO 2005/058132 A2 | 6/2005 |
| WO | WO 2008/060277 A2 | 5/2008 |

OTHER PUBLICATIONS

International Search Report and Written Opinion for corresponding PCT Application No. PCT/US2014/034743, dated Dec. 15, 2015, 23 pages.

* cited by examiner

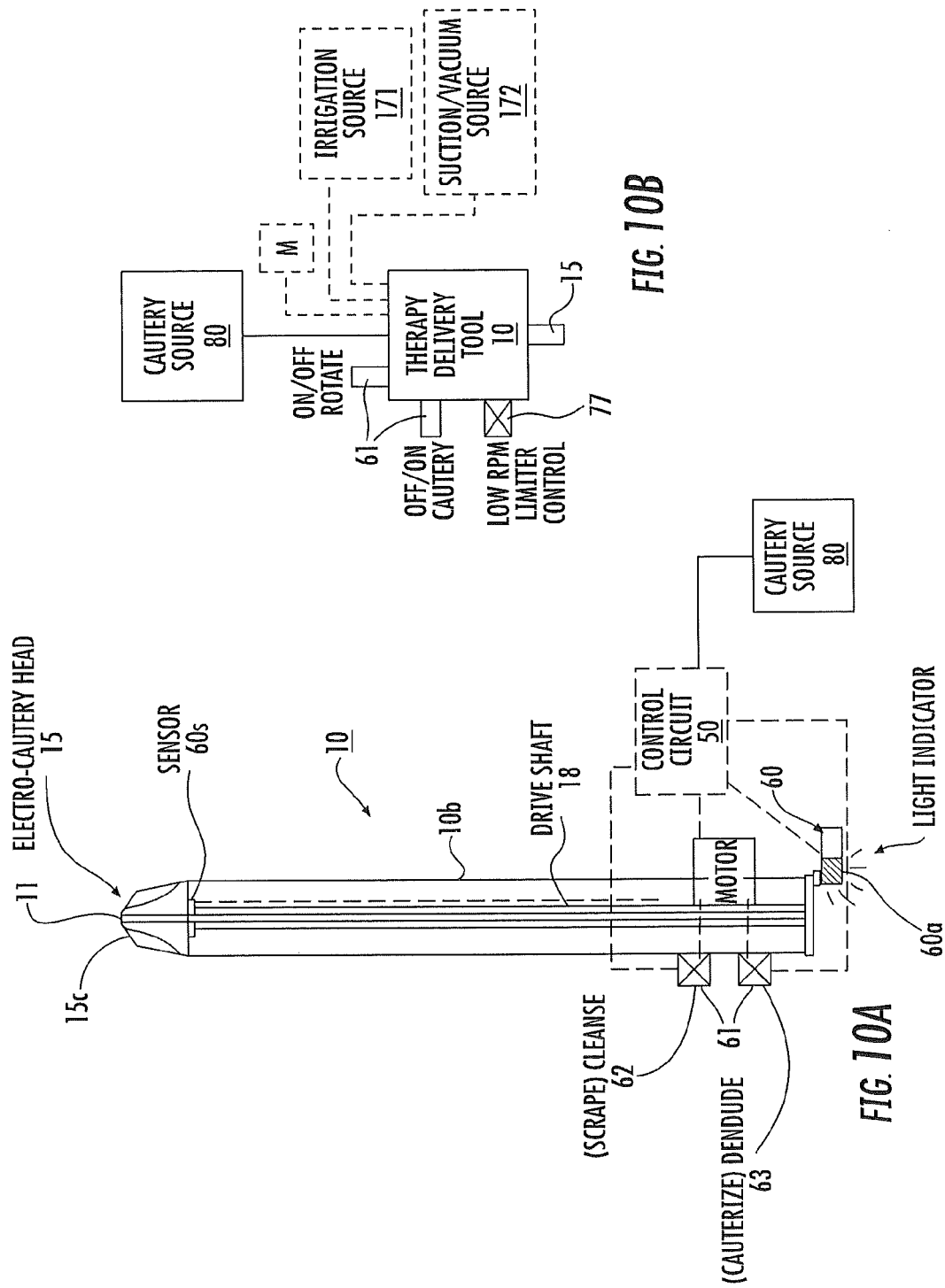

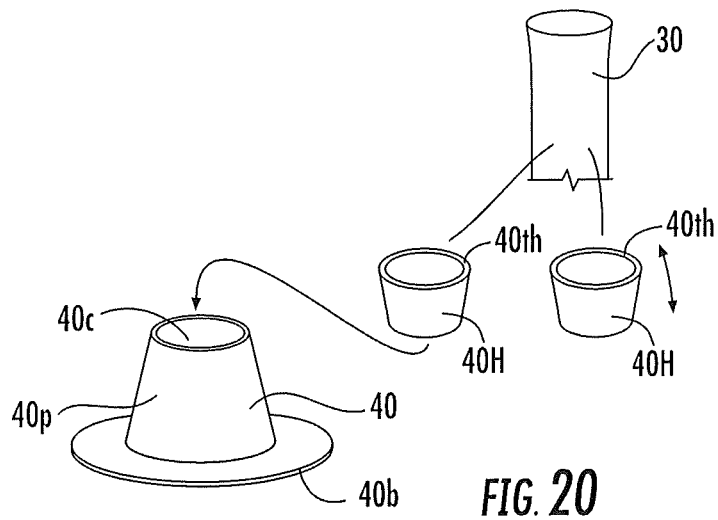
FIG. 20
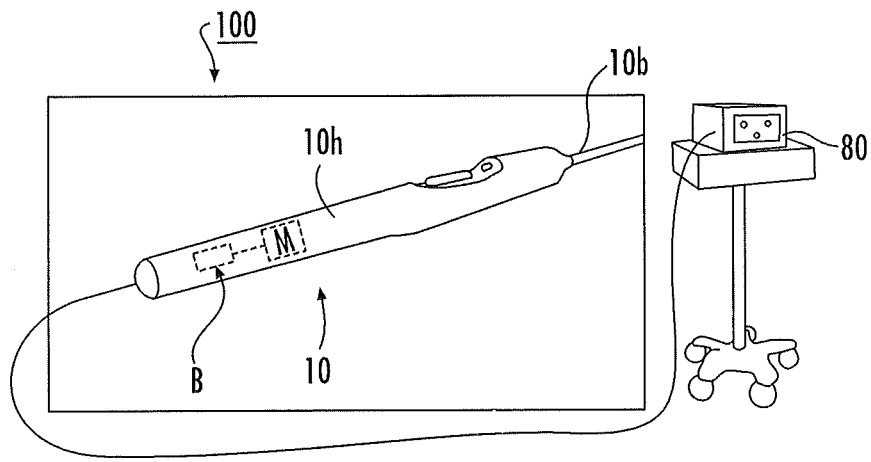
FIG. 21A
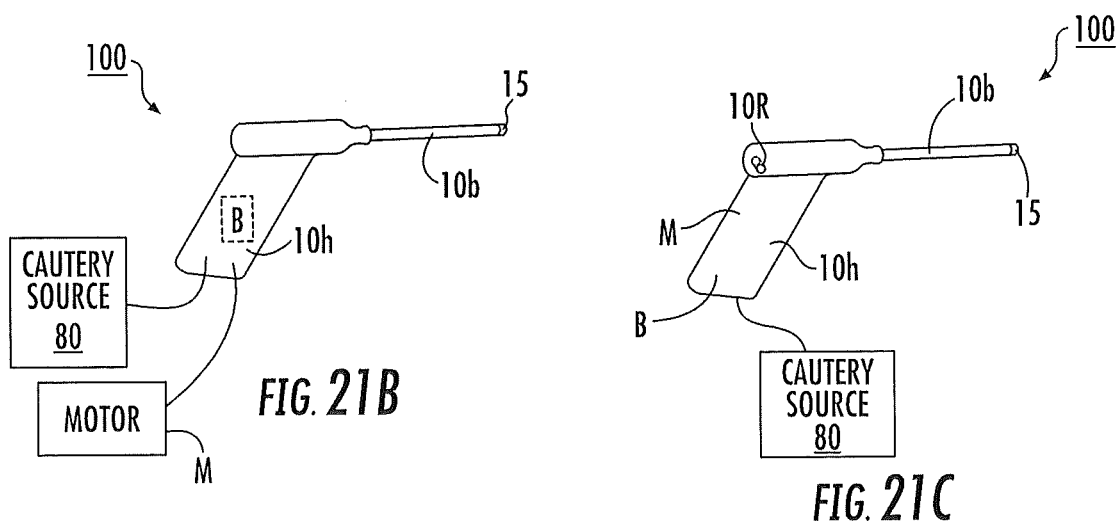
FIG. 21B
FIG. 21C

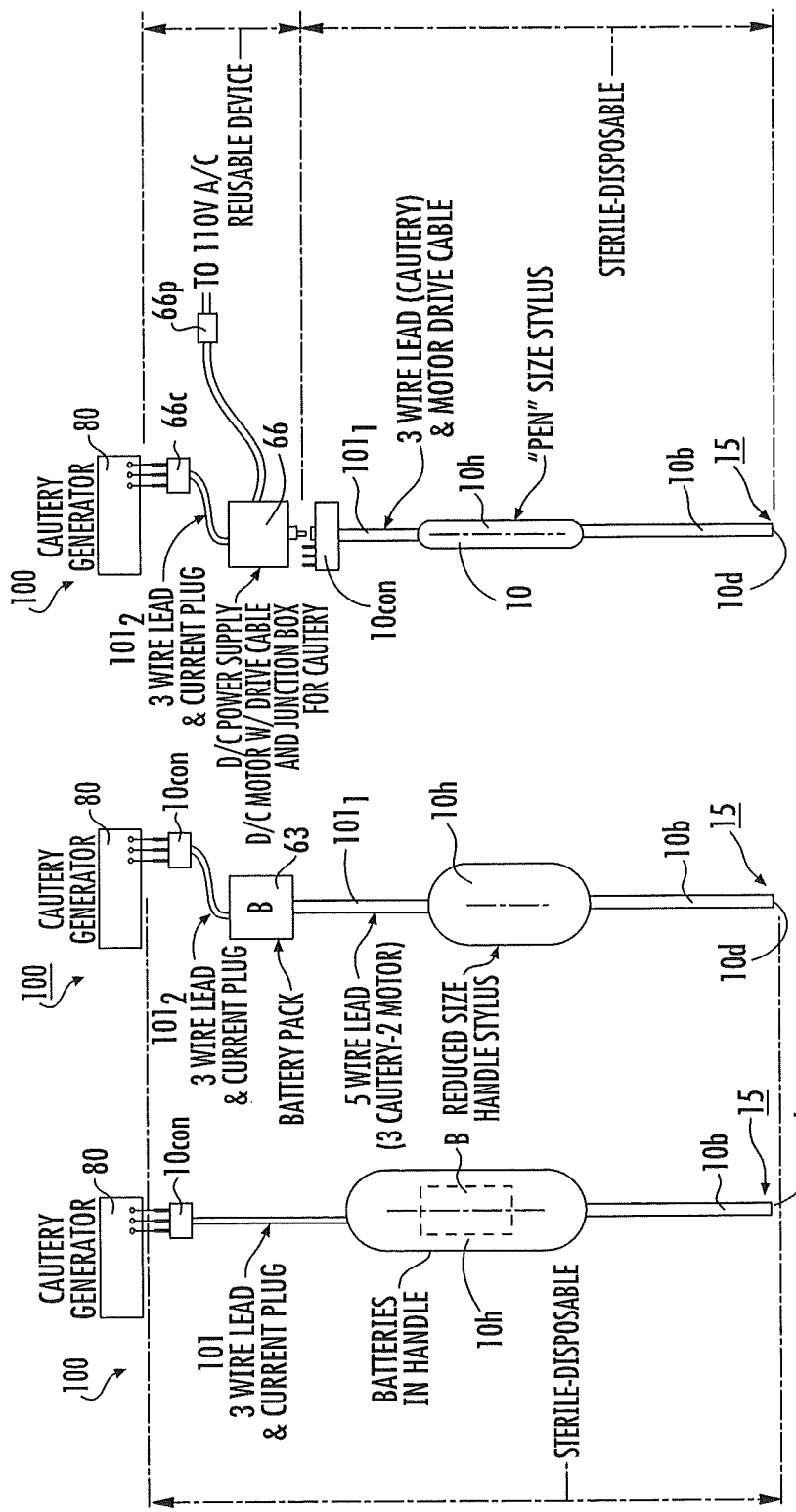

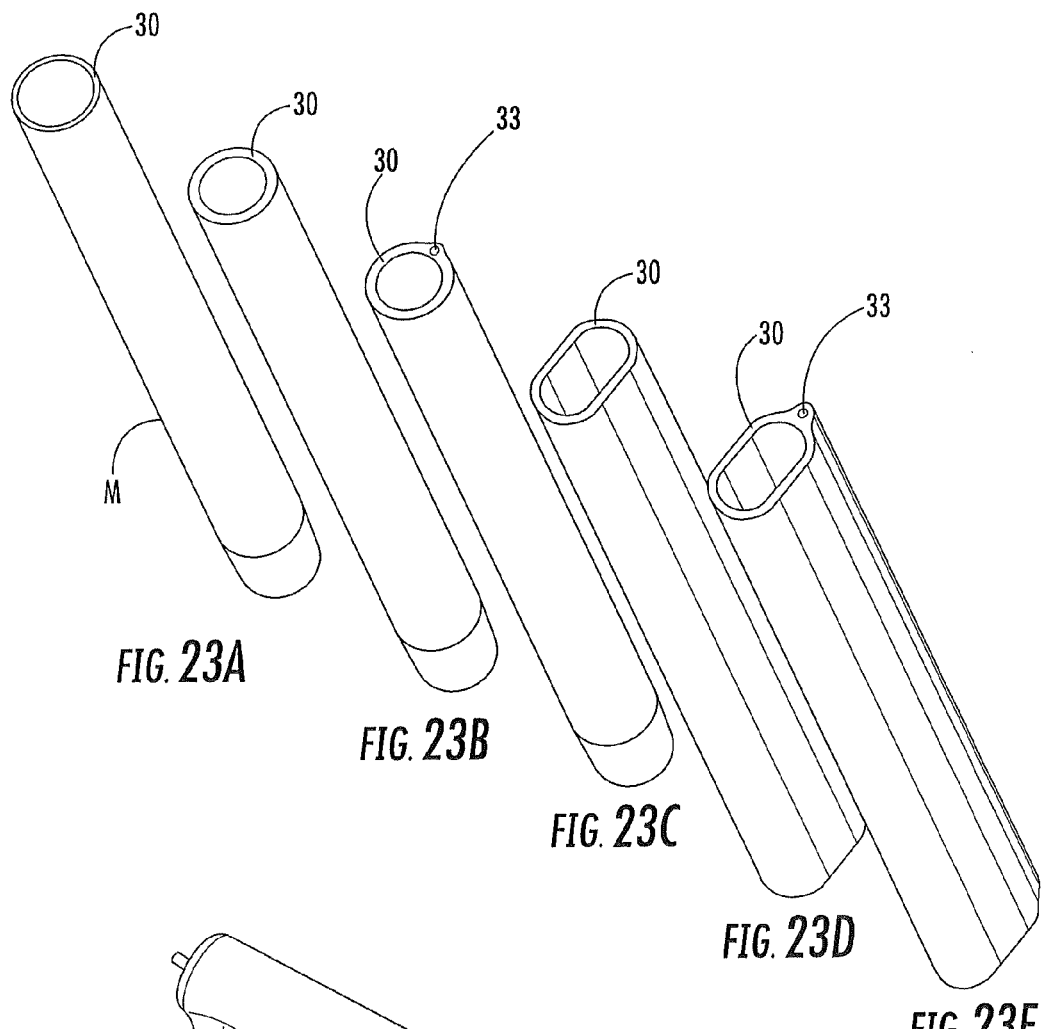
FIG. 23A
FIG. 23B
FIG. 23C
FIG. 23D
FIG. 23E
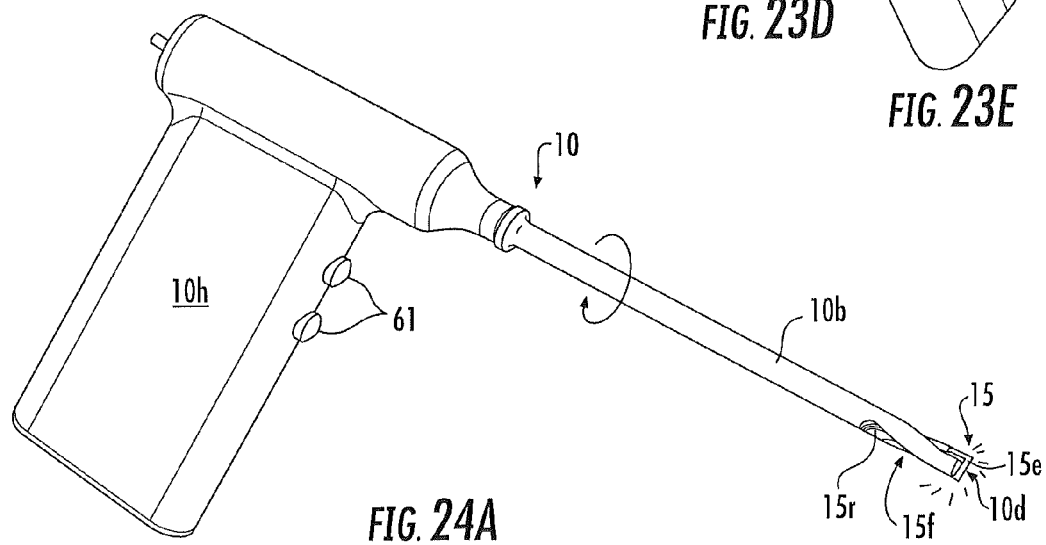
FIG. 24A

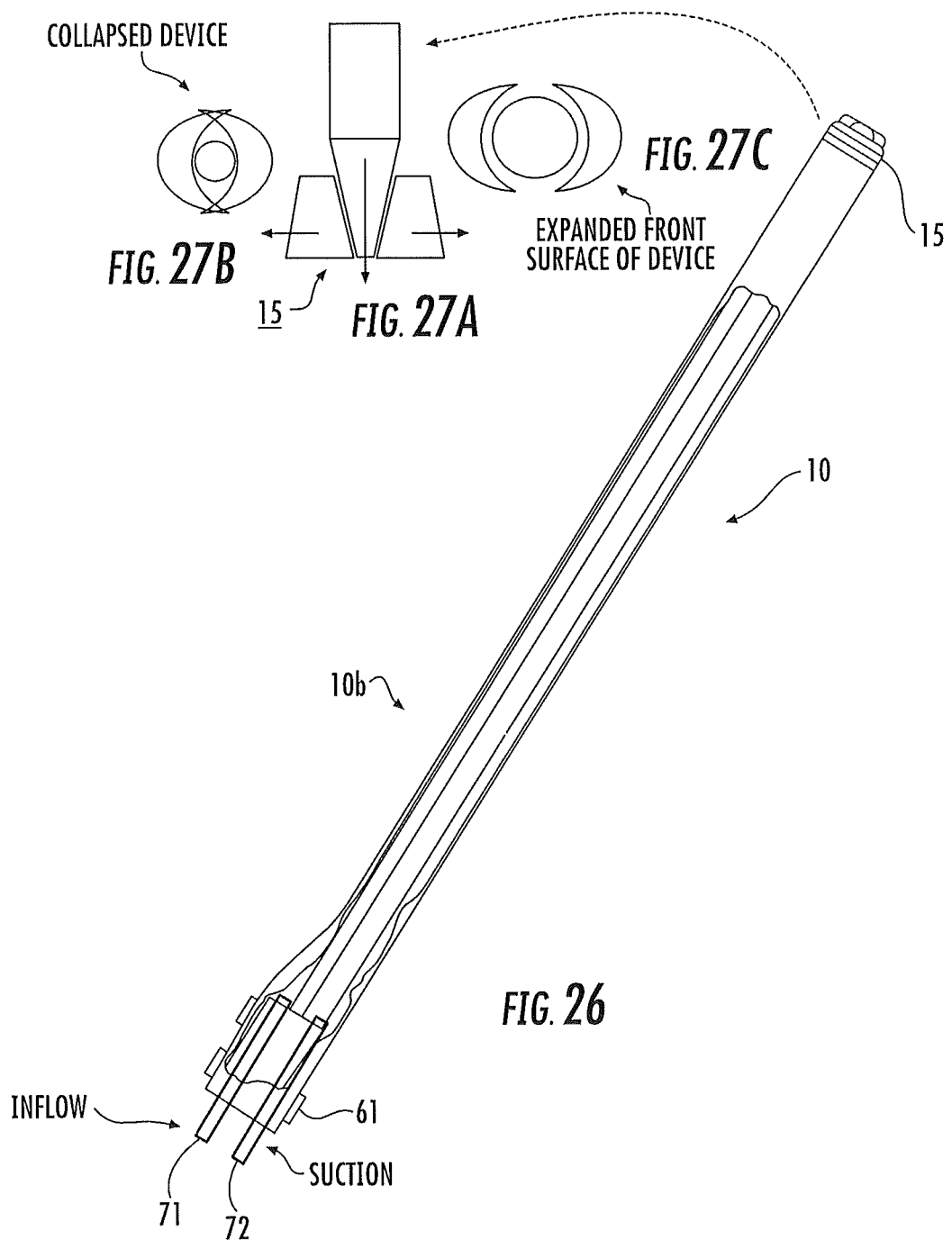

MINIMALLY INVASIVE METHODS FOR SPINAL FACET THERAPY TO ALLEVIATE PAIN AND ASSOCIATED SURGICAL TOOLS, KITS AND INSTRUCTIONAL MEDIA

RELATED APPLICATIONS

This application claims the benefit of and priority to U.S. Provisional Application Ser. No. 61/977,817, filed Apr. 10, 2014 and U.S. Provisional Application Ser. No. 61/815,416, filed Apr. 24, 2013, the contents of which are hereby incorporated by reference as if recited in full herein.

FIELD OF THE INVENTION

The present invention relates to spinal medical procedures.

BACKGROUND

The facet joint is unique in that it has innervations via a single nerve source. For many years, a process of facet joint rhizotomy (RFL) has been utilized to provide temporary relief of spinal arthritis pain. RFL procedures involve cryotherapy or radiofrequency techniques to either freeze or burn the nerve. RFL is temporary because the nerve is destroyed at a point between the dorsal root ganglion (the nerve cell's body) and the end plate receptors (pain stimulation points on the joint) and thus, like any peripheral nerve, the nerve gradually regenerates and the pain eventually returns. Most RFL procedures last between 4 and 8 months and must be repeated when the pain returns for the rest of the patient's life for effective pain relief. Another option involves spinal fusion which is an expensive and relatively complex surgery with a success rate of only around 50% for spinal arthritis and few spine surgeons would perform such a surgery for spinal arthritis. Spinal fusion involves inserting rods and screws into the spine to permanently lock the joints.

Alternatively, upon proper training, a facet treatment (which can be described as a debridement procedure) can be performed on a cervical, thoracic or lumbar facet joint of a human spine. During facet debridement, the synovial capsule between facets is removed so as to denude the bone and denervate the joint (preventing reinnervation).

In the past, it is believed that only a few surgeons have been able to carry out a facet debridement procedure. The procedure was carried out using a plurality of separate instruments including a long wire hand burr to denude tissue and a cauterization tool to cauterize remaining tissue. Cauterization may be needed to stop bleeding, to prevent regrowth of removed tissue, and/or for other purposes. This often means that a surgeon must revisualize the operative site after changing instruments and locate the area to be cauterized. This can be especially problematic in laparoscopic procedures. Specifically, the surgeon must remove the grinder or other mechanical cutting instrument from a cannula, insert a cauterization instrument, and then cauterize the appropriate region.

SUMMARY OF EMBODIMENTS OF THE INVENTION

Embodiments of the present invention provide relatively rapid, minimally invasive and cost effective treatments for long term, typically permanent, pain relief for spinal arthritis pain.

Some embodiments are directed to methods of minimally invasively treating a patient for back pain, including, for example spinal facet arthritis.

The method can be carried out as an outpatient procedure.

Some embodiments are directed to methods of treating a patient for back pain. The methods include: (a) inserting a guide pin into a patient to a target spinal facet joint; (b) sliding a dilation tube having a distal end with a tapered shape into the patient over the guide pin so that the dilation tube distal end resides adjacent the target spinal facet joint over a synovial capsule of the target spinal facet joint; (c) slidably advancing a cannula over the dilation tube so that a distal end of the cannula resides adjacent the target spinal facet joint; then (d) sliding the dilation tube rearward over the guide pin out of the patient while the cannula distal end remains adjacent the target spinal facet joint; then (e) inserting a combination debrider tool barrel having a denuding and cauterization head through the cannula in a straight path to the spinal facet joint; then (f) denuding and cauterizing soft tissue at the target spinal facet joint, serially or concurrently, using the denuding and cauterization head. The denuding is carried out by rotating the head of the combination debrider tool to remove an end plate receptor region comprising the synovial capsule of the spinal facet joint thereby treating back pain.

The denuding (and optionally the cauterizing) can be carried out by electronically rotating the denuding and cauterization head at a speed of between 10-5000 rpm.

The denuding can be carried out by electronically rotating the denuding and cauterization head at a speed of between about 10 to about 100 rpm.

The sliding the dilation tube, advancing the cannula, inserting the combination debrider tool, denuding and cauterizing and removing the tool, cannula and guide pin can be carried out in a short time of between about 3-15 minutes per target spinal facet joint.

The denuding can be carried out by automatically rotating the denuding and cauterization head electronically to remove soft capsular tissue and a superficial lining of the synovial capsule of the target spinal facet joint, then once the soft tissue is denuded, electronically rotating the tool head to contact an exposed outer surface of bone under the denuded tissue for a desired short time (e.g., seconds or a few minutes) to cleanse and/or scrape (e.g., polish) the exposed outer bone surface thereat without removing bone.

The denuding can be carried out so that the debrider tool head has an active rotation that has a duration of between about 30 seconds to about 2 minutes.

The cleansing can be carried out so that the debrider tool head rotates for a duration of between about 10 seconds to about 2 minutes.

The method can include placing an external stabilizer against skin of the patient over the target spinal facet joint before, during or after the inserting step, then inserting the cannula therein and locking the cannula to the stabilizer before the denuding and cauterizing.

The method can include tilting the cannula and elongate tool body held therein while held in the stabilizer to thereby treat a wider area of the target joint.

The denuding and cauterization head can include at least one electrically conductive linear cautery surface extending straight across a distal end thereof.

The denuding and cauterization head can have a fluted configuration with longitudinally extending curvilinear or straight flutes to inhibit tissue aggregation and/or clogging during the denuding and/or cauterization.

The denuding and cauterization head can have a fluted configuration with longitudinally extending curvilinear or straight flutes and a tissue contacting denuding and cauterization surface defined by radially extending linear segments separated by open gaps between adjacent linear segments.

The denuding and cauterization head can have an expandable operative configuration and the method can include, after the inserting step and before the denuding and cauterizing step, expanding the head to have a larger shape in a lateral direction relative to its shape during the inserting step.

The method can include electronically detecting when the denuding and cauterization head hits hard bone after denuding soft tissue and electronically generating an audible and/or visual output to a user.

The dilation tube can include first and second cooperating tubes, a first inner tube defining the tapered distal end and a second cooperating tube with a tapered forward end that resides upstream of the distal end of the inner tube over the first inner tube. The second tube can be shorter than the first tube and can abut and hold the cannula prior to the advancing step.

The sliding the dilation tube having a distal end with a tapered shape into the patient can be carried with the cannula attached thereto at a position upstream of the distal end of the dilation tube.

The target spinal facet joint can be a lumbar spinal facet joint and the cannula and debrider tool can extend out of the patient at an angle of between about 10-40 degrees laterally, perpendicular to the target spinal facet joint.

The target spinal facet joint can be a cervical or thoracic spinal facet joint and the cannula and debrider tool can extend out of the patient at an angle of between about 0-10 degrees laterally, perpendicular to the target spinal facet joint.

The inserting the guide pin can be carried out multiple times by inserting separate guide pins to different target spinal facet joints at a plurality of different levels, and wherein the inserting the guide pins into the target spinal facet joints is carried out prior to inserting a respective dilation tube at any level.

The inserting the guide pin into the patient can be repeated so that two pins extend bilaterally from a respective target spinal facet joint and the other method steps are carried out on both sides of the joint serially using the two pins to thereby denude and cauterize a respective target spinal joint bilaterally within about 10-15 minutes.

The combination tool and/or the cannula can include an axially and/or longitudinally extending guide pin channel that slidably extends over the guidewire.

The cannula can include a longitudinally extending guide pin channel that slidably extends over the guidewire and is parallel to the cannula cavity that holds the tool.

Other embodiments are directed to surgical tools for spinal facet surgical procedures for alleviating spinal pain (which may optionally be provided as a kit). The tools include: (a) a debrider tool having a distal end with a rotatable denuding and cauterization head, wherein the debrider tool comprises or is in communication with a motor that drives the rotatable denuding and cauterization head; (b) a dilation tube with a distal end having a tapered end, the dilation tube having a maximum outer diameter that is between about 5 mm to about 15 mm; and (c) a cannula sized and configured with a cavity having a width that is between about 5 mm to about 15 mm and is sized and configured to slidably receive at least a distal end portion of the debrider tool.

The dilation tube can include first and second cooperating tubes, a first inner tube defining the distal end and a second cooperating tube with a tapered forward end that resides upstream of the distal end of the inner tube over the first inner tube. The second tube can be shorter than the first tube and can slidably hold the cannula.

The cannula and/or the tool body can include an open guide pin channel with a width that is between about 0.75 mm and about 1.25 mm.

The debrider tool can include an elongate barrel portion that (a) is a monolithic member that defines a drive shaft that merges into the head or (b) defines an external wall that holds a drive shaft therein, the drive shaft being attached to the head, and wherein the elongate barrel portion is sized and configured to be slidably held in the cannula and has a maximal width that is between about 5 mm and about 15 mm.

The surgical tools can include an external stabilizer configured with a bottom surface that resides against skin of a patient and which has a cavity that holds the cannula in a fixed longitudinal position.

The stabilizer, where used, can be sized and configured to hold the cannula while allowing the cannula and distal end portion of the elongate body of the tool to tilt side to side and back to back, wherein the bottom surface of the stabilizer has a width that is between about 2-6 inches.

The debrider tool can include at least one longitudinally extending fluid channel for irrigation and/or suction.

The debrider tool can be configured to have a maximum rotation speed of between about 10 rpm to about 5000 rpm.

The debrider tool can be configured to have a maximum rotation speed of between about 10 rpm to about 100 rpm.

The surgical tools can be sterile and provided as a kit.

The debrider tool can comprise batteries to power the motor. The motor and batteries can be onboard the debrider tool. The debrider tool can include a cable with a connector that electrically connects the head to a cautery source.

The motor can be onboard the debrider tool. The tools can include a sterile battery pack attached to the debrider tool by a first sterile cable to power the motor. The surgical tools can include a second sterile cable that connects to the battery pack and a cautery source.

The motor can be held in a junction interface housing. The junction interface housing can include a direct current (DC) power supply that powers the motor. The junction interface housing can include a first cable that connects the junction interface housing DC power supply and a cautery source to the debrider tool, a second cable that connects the junction interface housing to the cautery source, and a third cable that connects the junction interface housing to an alternating current (AC) power source.

The cannula can include a longitudinally extending guide pin channel that is parallel to a cannula cavity that holds the elongate body of the debrider tool.

The denuding and cauterization head can include at least one electrically conductive linear cautery surface extending straight across a distal end thereof held by a non-conductive fluted shaft.

The denuding and cauterization head can have a fluted configuration with longitudinally extending curvilinear or straight flutes to inhibit tissue aggregation and/or clogging during the denuding and/or cauterization.

The denuding and cauterization head can have a fluted configuration with longitudinally extending curvilinear or straight flutes and a tissue contacting denuding and cauterization surface defined by radially extending linear segments separated by open gaps between adjacent linear segments.

The debrider tool denuding and cauterization head can have a first compact configuration and a second laterally expandable operative configuration that has a perimeter that is larger in at least a lateral dimension from the first compact configuration to thereby provide a compact insertion profile and/or a larger treatment surface area.

The debrider tool can include a monolithic metallic drive shaft that merges into the denuding and cauterization head and that is sized and configured to be slidably held in the cannula. The denuding and cauterization head can include a tissue contacting denuding and cauterization surface defined by radially extending linear segments separated by gap spaces between adjacent linear segments.

The debrider tool can include an elongate barrel portion that defines an external wall that holds a drive shaft therein. The drive shaft can have a non-conductive distal end portion that is fluted and holds an electro-cautery member that together define the denuding and cauterization head. The elongate barrel portion can be sized and configured to be slidably held in the cannula and has a maximal width that is between about 5 mm and about 15 mm.

Still other embodiments are directed to spinal facet therapy systems to alleviate pain. The systems include: (a) a cautery source; (b) a spinal facet therapy tool with an elongate barrel having a rotatable head in communication with the cautery source and configured to automatically rotate at between about 10 rpm to about 5000 rpm during denuding and/or cleansing of respective spinal facet joints to remove an end plate receptor region comprising the synovial capsule of the spinal facet joint thereby treating back pain; (c) a dilation tube; and (d) a guide cannula configured to hold the elongate barrel therein while allowing the distal end of the tool with the rotatable head to extend out therefrom during active treatment.

The rotatable head can include at least one electrically conductive linear cautery surface extending straight across a distal end thereof held by a non-conductive fluted shaft.

The rotatable head can have a fluted configuration with longitudinally extending curvilinear or straight flutes to inhibit tissue aggregation and/or clogging during the denuding and/or cauterization.

The rotatable head can have a fluted configuration with longitudinally extending curvilinear or straight flutes and a tissue contacting denuding and cauterization surface defined by radially extending linear segments separated by open gaps between adjacent linear segments.

The rotatable head can have a first compact configuration and a second laterally expandable operative configuration with a perimeter that has at least a lateral dimension that is larger than the compact configuration to thereby provide a compact insertion profile and/or a larger treatment surface area.

The spinal facet therapy tool can have a monolithic metallic drive shaft that merges into the rotatable head and that is sized and configured to be slidably held in the guide cannula, wherein the drive shaft has a maximal width that is between about 5 mm and about 15 mm.

The spinal facet therapy tool can have an elongate barrel portion that defines an external wall that holds a drive shaft therein. The drive shaft can have a non-conductive distal end portion that is fluted and holds an electro-cautery member that together define the denuding and cauterization head. The elongate barrel portion can be sized and configured to be slidably held in the cannula and has a maximal width that is between about 5 mm and about 15 mm.

Still other embodiments are directed to instructional media for facilitating or training surgeons to carry out a spinal debridement procedure for spinal arthritis pain. The media includes a video or instructional manual showing a sequence of surgical steps to carry out a spinal debridement procedure using a spinal facet debridement tool that both denudes and cauterizes synovial capsule tissue. The video and/or instructional manual shows, illustrates or describes any or all of the methods described herein and/or demonstrates operation of the surgical tools described herein.

Yet other embodiments are directed to spinal facet surgical tools. The tools include a tool housing with (a) an elongate barrel having a distal end with a rotatable denuding and cauterization head, (b) a drive shaft extending in the elongate barrel attached to the rotatable denuding and cauterization head; (c) a motor in communication with the shaft to drive the rotatable curved denuding and cauterization head; (d) a sensor in communication with the shaft and/or the rotatable curved denuding and cauterization head for detecting when the head contacts hard bone during a denuding operation; and (e) a control circuit that generates an auditory or visual output to a user when the rotatable head hits bone.

The sensor can include a strain gage, an optical sensor or a torque sensor.

The tool can be configured to have a maximum rotational speed of between about 10 rpm to about 5000 rpm.

The tool can be configured to have a maximum rotational speed of between about 10 to about 100 rpm.

The denuding and cauterization head can have a first compact configuration and a second laterally expandable operative configuration with a perimeter with at least a lateral dimension that is larger than the compact configuration to thereby provide a compact insertion profile and/or a larger treatment surface area.

Still other embodiments are directed to spinal facet surgical tools that include: a debrider tool with an elongate body portion having a distal end with a rotatable denuding and cauterization head. The denuding and cauterization head has a first compact configuration and a second laterally expandable operative second configuration to thereby provide a compact insertion profile and/or a larger treatment surface area, wherein, in the first compact configuration the head has a maximal width of between about 5-15 mm; a drive shaft extending in the debrider tool elongate body attached to the rotatable denuding and cauterization head; a motor in communication with the shaft to drive the rotatable curved denuding and cauterization head; and a power source in communication with the motor. The power source can include one or more of the following: (i) batteries in a handle of the debrider tool; (ii) a battery pack attached to the elongate body via a cable; or (iii) a direct current (DC) power source in a junction interface housing.

The power source can include only the onboard batteries to power the motor. The drive shaft can rotate at a maximum rpm of between about 10-100.

The denuding and cauterization head can have a fluted configuration.

The denuding and cauterization head can have a curved head that tapers from a tip having a narrow peak region that surrounds a center aperture that merges into the guide pin receiving channel to a wider region away from the tip. The curved head can have a shape that substantially conforms to a shape of the facet joint.

Typically, the angulation of the debrider tool and/or cannula and guide wire is defined so as to be perpendicular to the facet joint surface, which is usually 10 to 40 degrees laterally in the lumbar region and 0 to 10 degrees laterally in the thoracic and cervical regions.

Other embodiments are directed to surgical kits and/or surgical tools for spinal facet surgical procedures for spinal arthritis pain.

The tool can have a user input to allow a user to electronically select a tissue denude run mode and a cleanse run mode. The cleanse run mode can have a lower speed (rpm) than the tissue denude run mode.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

Other systems and/or methods according to embodiments of the invention will be or become apparent to one with skill in the art upon review of the following drawings and detailed description. It is intended that all such additional systems, methods, and/or devices be included within this description, be within the scope of the present invention, and be protected by the accompanying claims.

BRIEF DESCRIPTION OF THE DRAWINGS

Other features of the present invention will be more readily understood from the following detailed description of exemplary embodiments thereof when read in conjunction with the accompanying drawings.

FIG. 10A is a schematic illustration of a debridement system tool that may include an external visual and/or auditory indicator that can indicate when the denuding of capsule tissue at the spinal facet joint is complete according to embodiments of the present invention.

FIG. 10B is a schematic illustration of another debridement system according to embodiments of the present invention.

FIG. 20 is a schematic illustration of yet another embodiment of a stabilizer device according to embodiments of the present invention.

FIG. 21A is a schematic illustration of a therapy system according to embodiments of the present invention.

FIG. 21B is a schematic illustration of another embodiment of a therapy system according to embodiments of the present invention.

FIG. 21C is a schematic illustration of another embodiments of a therapy system according to embodiments of the present invention.

FIGS. 22A-22C are schematic illustrations of embodiments of different therapy system configurations according to embodiments of the present invention.

FIGS. 23A-23E are side perspective illustrations of exemplary guide/working cannulas according to embodiments of the present invention.

FIG. 24A is n enlarged side perspective view of an exemplary spinal facet debridement therapy tool according to embodiments of the present invention.

FIG. 26 is a partial cutaway view of a therapy tool with suction and irrigation fluid paths according to embodiments of the present invention.

FIGS. 27A-27C are schematic illustrates of a laterally expandable distal end of a therapy tool according to embodiments of the present invention.

DETAILED DESCRIPTION OF EMBODIMENTS OF THE INVENTION

Figure 1:
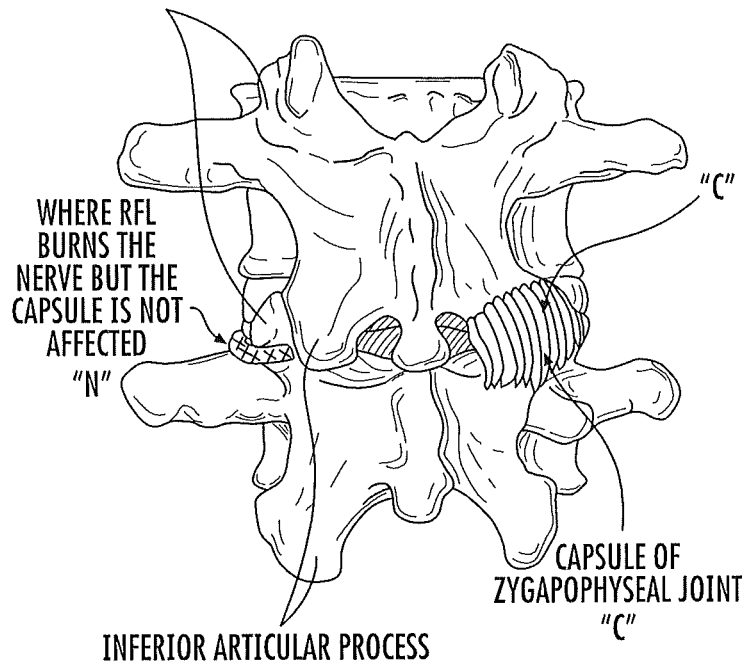
FIG. 1 is a schematic illustration of a typical lumbar segment with a spinal facet joint illustrating an exemplary RFL location of a nerve (the nerve to the joint is shown on the left in hatched line without the capsule) in contrast to a target facet joint debridement of an end plate receptor region which includes a synovial capsule of the joint (e.g., a capsule of zygapophyseal joint).

The present invention now is described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. Broken lines illustrate optional features or operations unless specified otherwise. One or more features shown and discussed with respect to one embodiment may be included in another embodiment even if not explicitly described or shown with another embodiment.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention. The sequence of operations (or steps) is not limited to the order presented in the claims or figures unless specifically indicated otherwise. In the claims, the word "a" with respect to an element is intended to include one or more of such elements and is not limited to a single such element unless stated otherwise.

The term "about" means that the recited number or value can vary by +/−20%.

The term "sterile" means that the noted device or material meets or exceeds defined medical guidelines of cleanliness as is well known to those of skill in the art to be substantially (if not totally) without contaminants so as to be suitable for medical uses and/or comply with defined medical guidelines, rules and/or regulations.

Embodiments of the invention are suitable for human or animal use, and are particularly suitable for human use.

The term "instructional media" refers to electronic and/or paper manuals, videos, user guides, or the like illustrating and/or describing operation of the debridement tool and/or the spinal facet debridement surgical procedure.

The term "fluted" and derivatives thereof refer to recesses, typically flat or concave grooves, on one or more of the inner wall, outer wall, or shaft of a barrel, drive shaft, rotatable head or column of a surgical tool.

The term "denudement" and derivatives thereof refer to a procedure to polish, (gently) grind, scrape, file, grate, cleanse and/or rasp away soft tissue of facet joints to thereby denude tissue and uncover or expose the underlying bone without cutting into or removing the bone (e.g., in contrast to a sharp cutting edge like a knife). The denudement tool can have a surface that has an abrasive texture and/or configuration which may include small teeth.

The term "debridement" and derivatives thereof refer to the removal of soft tissue associated with an end plate receptor region of a target spinal facet joint including the synovial capsule and tissue scraping of an outer boney surface of the joint.

Generally stated, embodiments of the invention allow spinal facet joint debridement to remove the end plate receptor region which includes the synovial capsule and outer surface of the joint. Once the synovial capsule and outer surface of the joint are denuded, the nerves have nowhere to re-adhere to the joint and thus the joint is permanently denervated (communication between the facet joint and the brain is gone). In studies carried out by the inventor, pain relief is permanent in 75-80% of patients.

While the joint continues to have arthritis, the patient's perception of the pain is gone as pain is what the brain perceives it to be and the patient simply does not feel the spinal pain. The joints have no worse decay then they would with the currently utilized RFL procedure since both utilize a denervation technique where the pain signals are severed between the brain and the joint.

Advantageously, while the current RFL procedure is a temporary treatment of pain, the spinal facet debridement procedure is a permanent alleviation of pain at the treated spinal facet joint. Thus, the spinal facet debridement procedure is cost effective. For example, currently, people who undergo RFL procedures may have them performed around twice a year for the duration of their lives, while the spinal facet debridement procedure is done once for the affected area. As people age, they may need other areas of the spine treated; for example, a person who has a low back debrided may eventually need the neck debrided. This is similar to the current RFL, in which only a small segment of the spine is done at one time for both patient comfort and time constraints. Usually two or three levels, bilaterally, are performed for either procedure.

Figure 2:
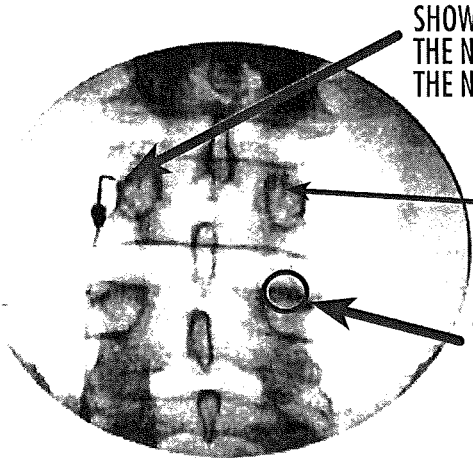
FIG. 2 is a X-ray image of a spinal facet joint illustrating needle placement for an RFL procedure to burn the nerve in contrast to placement of a debrider portal (shown as a circle on the right side of the image) for a target region denuded by a single combination abrasion and cauterization tool to remove the capsule according to embodiments of the present invention.

Referring now to the figures, FIG. 1 illustrates an RFL treatment for nerve "N" (hatched line on left) and also illustrates the synovial capsule "C" on the right. FIG. 2 is an X-ray of a patient showing an RFL procedure where the needle is placed to burn the nerve (top left arrow). FIG. 2 also illustrates an approximate size of a region of a target spinal facet joint (circle on right side of figure) that can be denuded by the therapy delivery tool 10 (e.g., FIGS. 5A, 6A) to remove the capsule "C" and thus prevent the nerve from renervating.

Figure 5A:
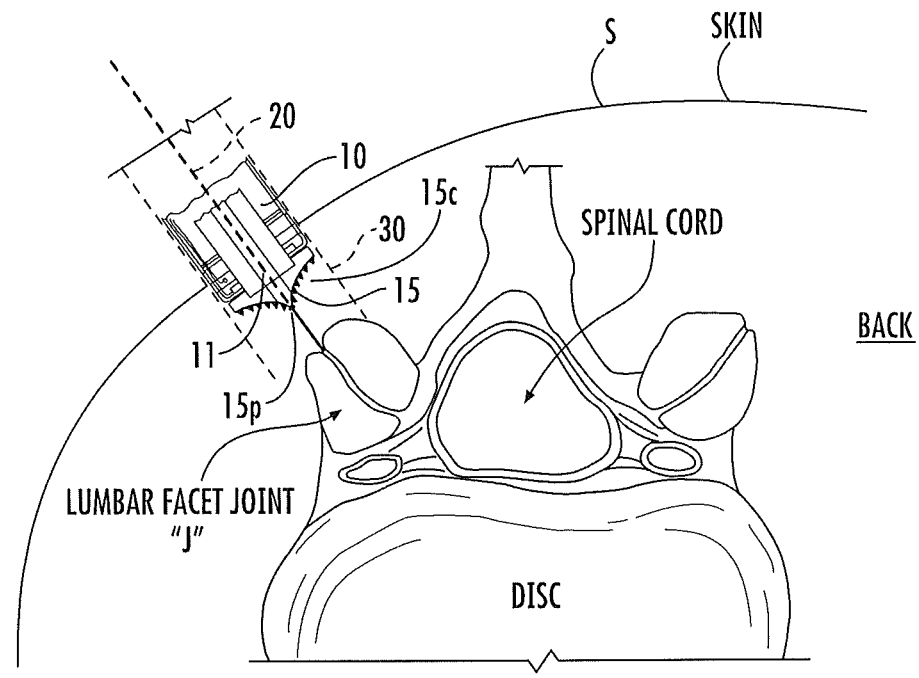
FIG. 5A is a section view of a lumbar facet joint with a combination tissue removal and cauterization debridement tool inserted over the guide pin in the cannula to a lumbar facet joint according to embodiments of the present invention.
Figure 6A:
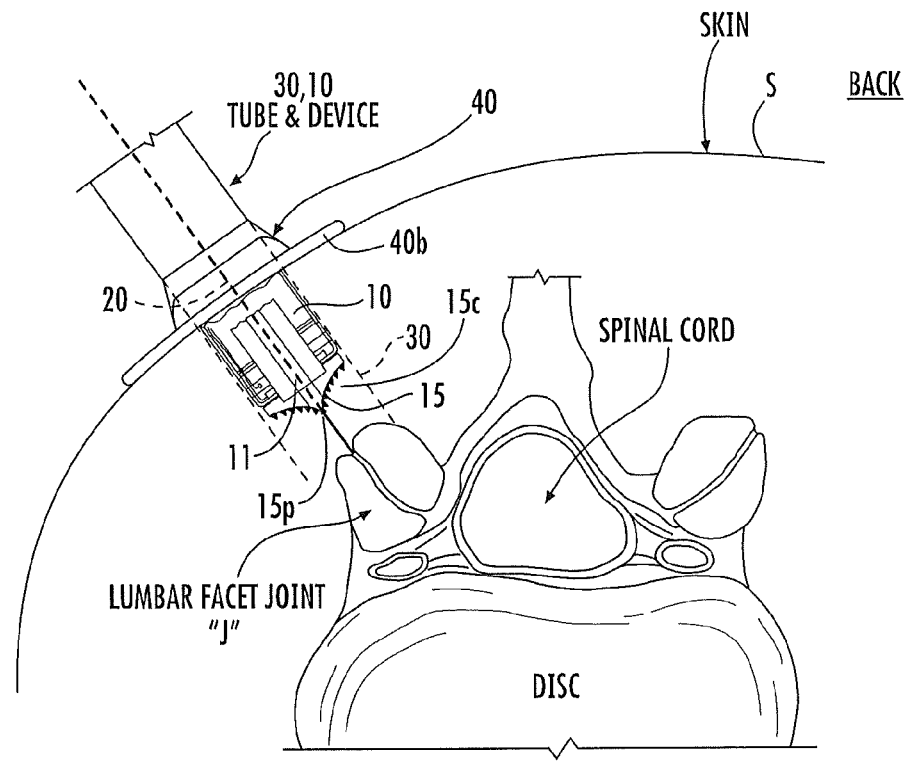
FIG. 6A is a section view of a lumbar facet joint with a combination tissue removal and cauterization debridement tool in a working cannula held by an external stabilizer to reside proximate a lumbar facet joint according to embodiments of the present invention.

As shown in FIGS. 5A and 6A, the spinal facet therapy delivery (e.g., "debrider") tool 10 has a head 15 that contacts target tissue. The head 15 can optionally have a curved outer surface 15c that faces the facet joint surface J. The head 15 can have a distal end with a surface that optionally tapers in to a peak region 15p centered around an aperture 11a that merges into the pin receiving channel 11. As shown in FIGS. 5A and 6A, the curvature of the curved surface 15c can substantially correspond to the curvature of the target spinal facet joint. FIGS. 25A-25G illustrate other embodiments of the rotatable debrider therapy head 15.

In some embodiments, the head 15 can have an electroconductive member and/or outer surface to which electrical energy is supplied (in bipolar or monopolar mode), thereby permitting the head 15 to cauterize tissue. The electrocauterization can be any suitable cautery source, typically RF power, although other electrical sources may be used. For additional discussion of components of a suitable combination spinal facet debrider tool 10, see, e.g., U.S. Pat. No. 8,167,879, the contents of which are hereby incorporated by reference as if recited in full herein.

It is contemplated that other types of ablation/cauterization may be used including ultrasound (including, for example "high-intensity focused ultrasound" or "HIFU"), microwave, cryoablation, laser ablation, and the like.

Figure 24B:
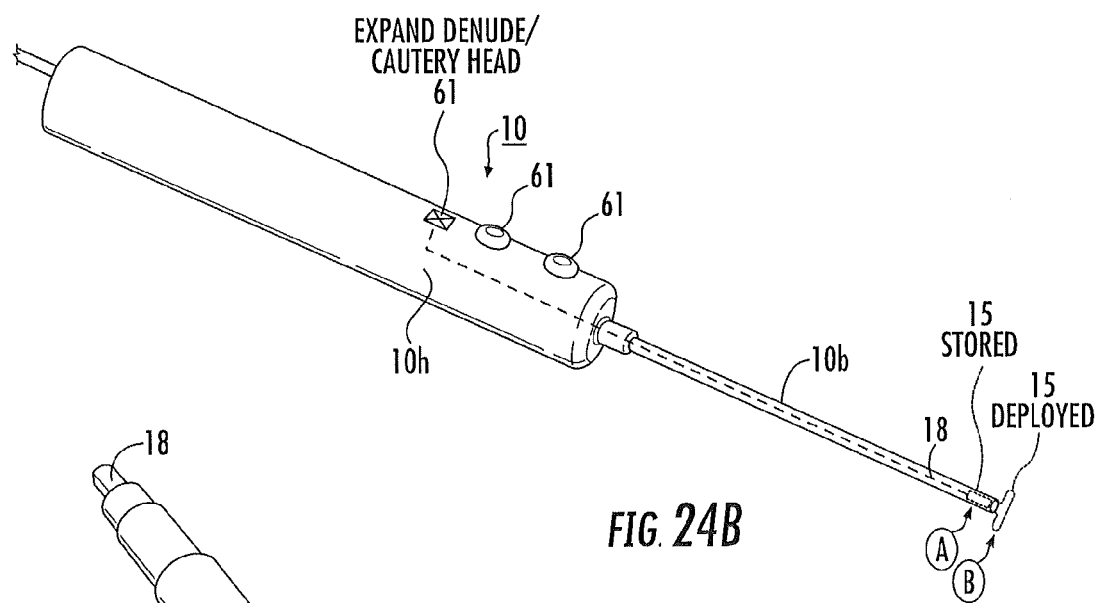
FIG. 24B is n enlarged side perspective view of another exemplary spinal facet debridement therapy tool according to embodiments of the present invention.

The distal end portion of the therapy delivery tool 10 with the head 15 can have a maximal outer diameter that is between about 5-15 mm, such as about 5 mm, about 6 mm, about 7 mm, about 8 mm, about 9 mm, about 10 mm, about 11 mm, about 12 mm, about 13 mm, about 14 mm and about 15 mm, typically between 10-12 mm. The distal end portion of the tool 10d can have a laterally collapsible/retractable shape and may slidably reside inside a tool outer sheath between an internal position A and a deployed position B as shown in FIG. 24B as will be discussed further below.

The procedure can be done via conscious sedation and local anesthesia or general anesthesia as per the surgeon's and patient's preference. For, example, conscious sedation can be used with a remifentanyl mixture. The spinal region is typically prepped and draped accordingly. Utilizing fluoroscopic or other suitable imaging guidance, the facet joints J that may be treated can be identified.

Figure 3:
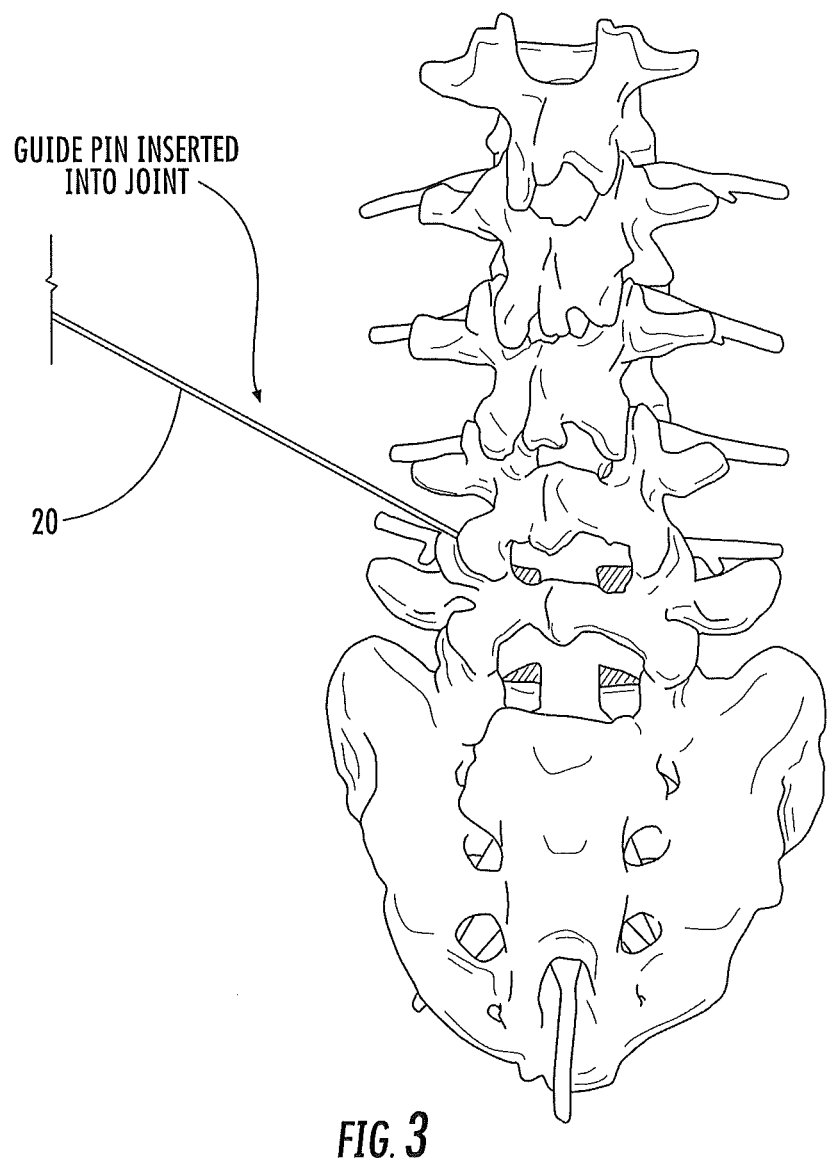
FIG. 3 is a front view of a model of the spine illustrating a guide pin in position in a spinal facet joint according to some embodiments of the present invention.

To facilitate a minimally invasive treatment, as shown in FIG. 3, a rigid guidewire and/or pin 20 (e.g., a Steinman pin) with a diameter of approximately 1 mm can be inserted through skin S and tissue of a patient into the target facet joint region J. The guidewire/pin 20 can be tapped into place with a small hammer or other suitable device. A small incision, typically between about 0.25-1 inch, e.g., about ½ inch or about ¾ of an inch can be made about the pin 20. In other embodiments, the incision can be made before or during the insertion of the pin 20.

Figure 4A:
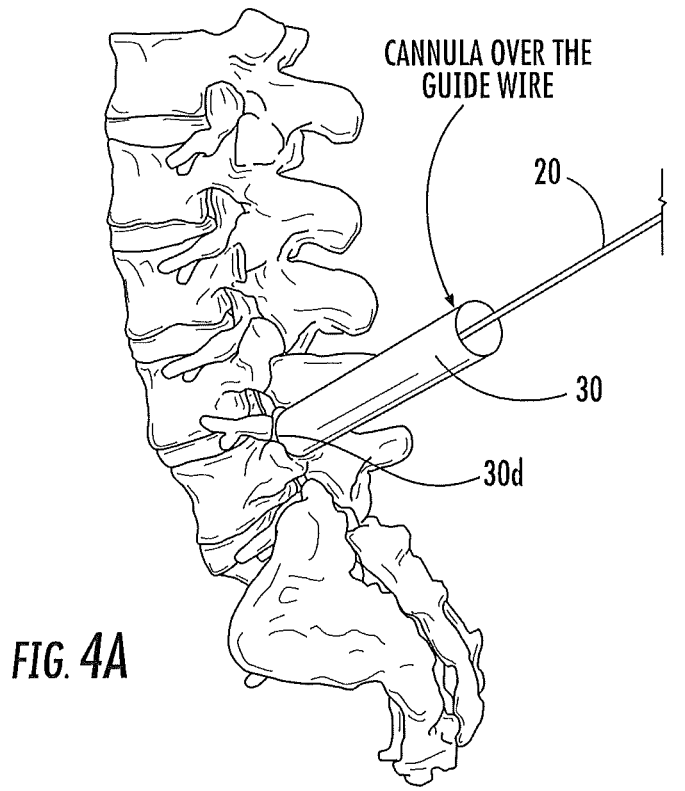
FIG. 4A is a side view of the model and guide pin shown in FIG. 3 with a guide cannula extending down to a the target spinal facet joint according to some embodiments of the present invention.
Figure 4B:
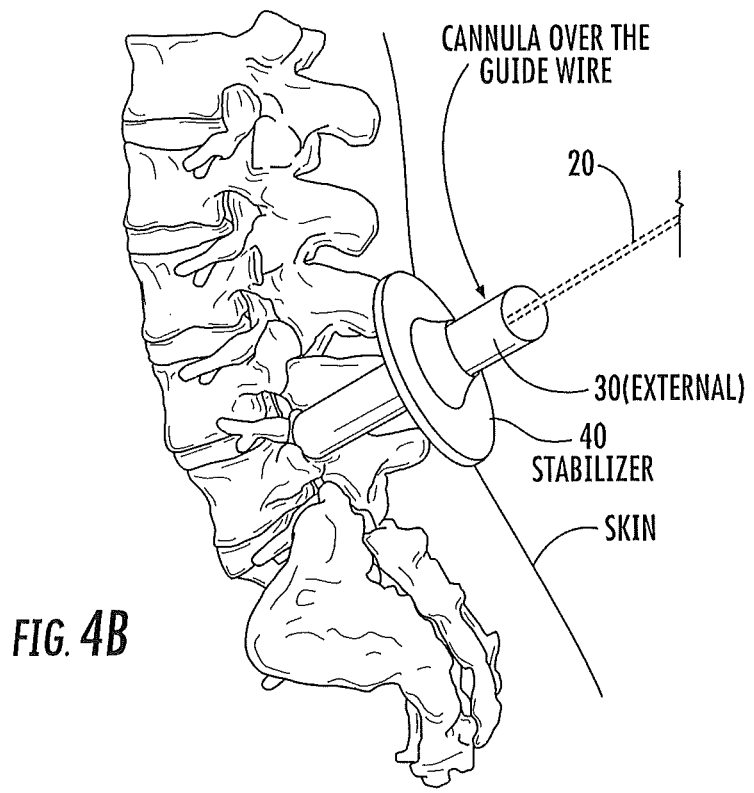
FIG. 4B is a side view of the model shown in FIG. 3 with a guide cannula held by a cooperating stabilizer according to embodiments of the present invention.

As shown in FIGS. 4A and 4B, a guide cannula 30 (sometimes also called "a working cannula") can be inserted into the patient so that a distal end thereof 30*d* resides proximate the target facet site J. As shown in FIG. 4A, the guide cannula 30 can be inserted using the guide pin 20 to help position the guide cannula in the body. FIG. 4B illustrates the use of an external stabilizer 40 that holds the guide cannula 30. The guidewire/pin 20 may be removed before or after placement of the stabilizer 40 (where an optional external stabilizer is used).

Figure 5B:
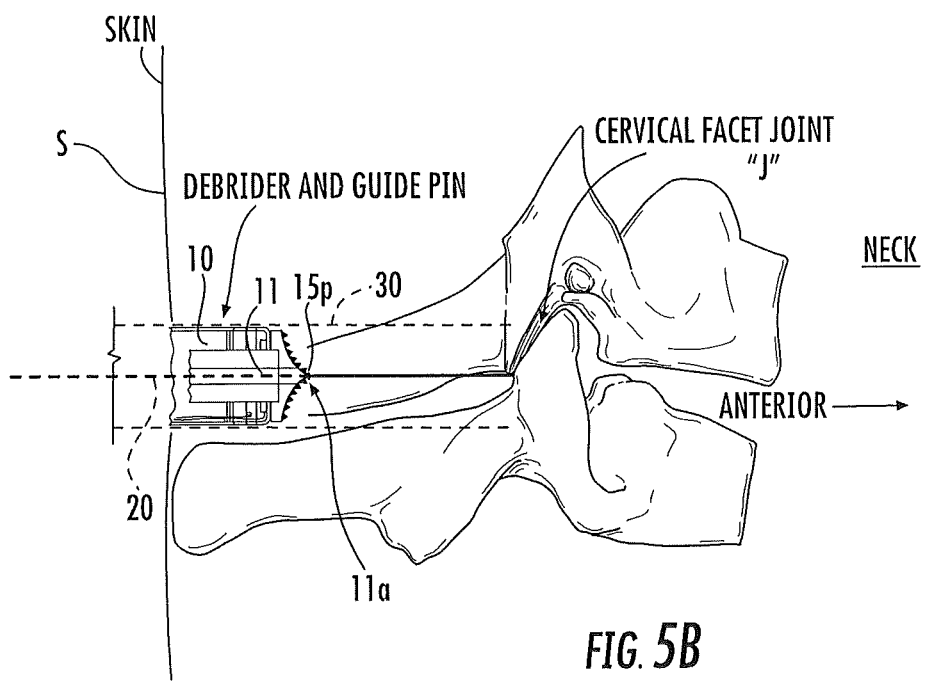
FIG. 5B is a lateral view of a cervical facet joint illustrating the combination debridement tool in the cannula over the guide pin according to embodiments of the present invention.
Figure 6B:
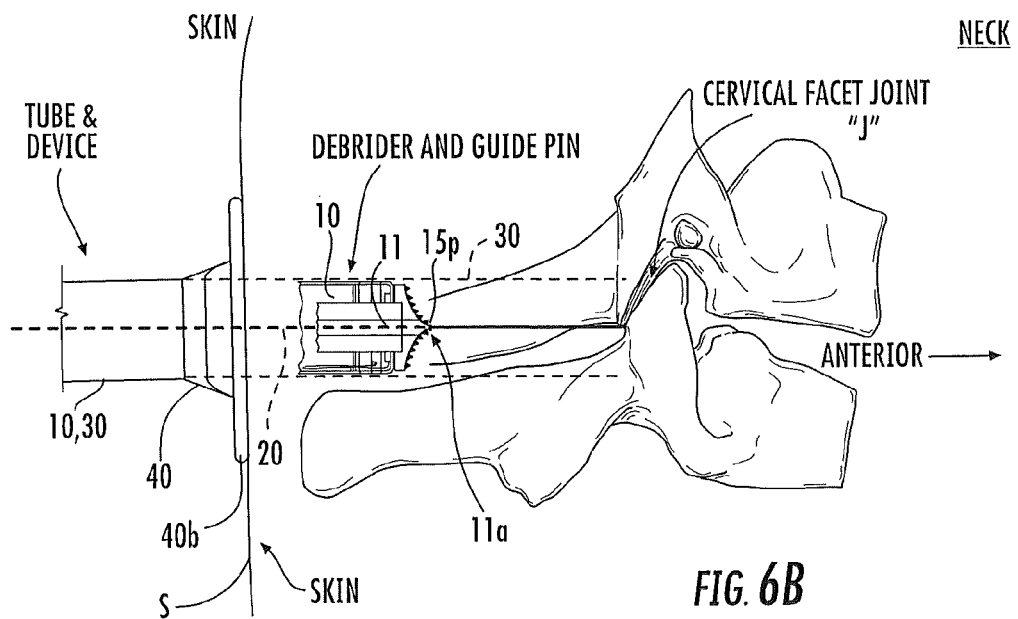
FIG. 6B is a lateral view of a cervical facet joint illustrating the combination debridement tool in the working cannula held by a stabilizer according to embodiments of the present invention.

FIGS. 5A, 6A and 5B, 6B illustrate that the same debrider tool 10 can be used to treat different spinal facet joints. FIGS. 5A and 6A illustrate the debrider tool at a lumbar facet joint J and FIGS. 5B and 6B illustrate at a cervical facet joint J.

The term "stabilizer" refers to a device that is configured to provide one or both of a depth stop for the therapy delivery tool 10 and/or rotational stabilization for the tool 10 proximate the skin entry site S. The stabilizer device 40 can slidably receive and releasably hold the guide cannula 30 and/or tool 10 and may be used without requiring the guide pin 20, e.g., the guide pin 20 may not be used or may be withdrawn prior to or after the stabilizer 40 is in position on the patient while holding the guide cannula 30 at a desired stop depth as will be discussed further below.

As shown in FIGS. 4B, 6A and 6B, the stabilizer 40 can have a bottom 40*b* that resides against skin S of the patient, either directly or indirectly. The bottom 40*b* can have a width W (FIGS. 12A, 13) of between about 2-6 inches, typically between about 3-5 inches, such as about 3 inches, about 3.5 inches, about 4 inches, about 4.5 inches and about 5 inches. The bottom 40*b* can have a larger width than the width of the primary body 40*p* that has the through-channel 40*c* for the guide cannula 30 and/or tool 10. The stabilizer 40 typically has a smaller height than the barrel 10*b* (FIGS. 9G, 14) of the therapy delivery tool 10 and/or guide cannula 30. In some particular embodiments, the stabilizer 40 can have a height that is between about 2-10 inches, typically between about 3-6 inches, such as about 3 inches, about 3.5 inches, about 4 inches, about 4.5 inches, about 5 inches, about 5.5 inches, and about 6 inches, although the stabilizer may have other height dimensions.

Figure 7A:
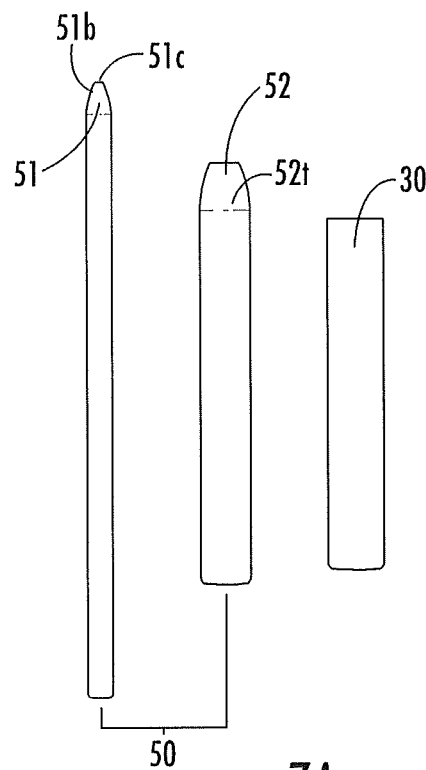
FIG. 7A is a top view of three disassembled cooperating tissue dilation components suitable for use in a debridement procedure according to embodiments of the present invention.
Figure 7B:
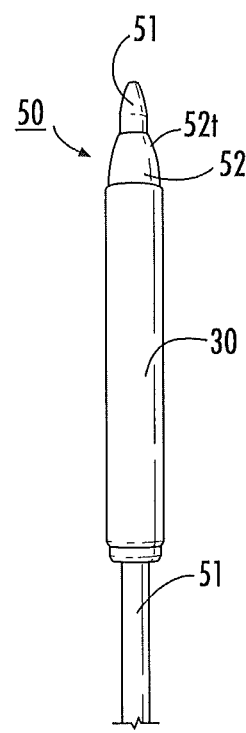
FIG. 7B is an assembled view of the three components shown in FIG. 7A.

In some embodiments, a dilation tube 50 (FIGS. 7A, 7B) can be fed over the guide pin 20, typically after the guide pin distal end is anchored to the treatment site of the facet joint J. As shown in FIG. 7A, the dilation tube 50 can be configured with a plurality of cooperating components including an inner tube 51 with a distal end having a tapered end (e.g., a bullet-like shape) 51*b*. The tapered (bullet shaped) end 51*b* can be inserted down to the facet joint J. The tapered end 51*b* can be sized and configured to push through the muscle to create an opening, preferably without cutting the muscle. The inner tube 51 can include a center bore 51*c* that receives the guide pin 20. The dilation tube 50 may include a second tube 52 with a distal tapered end 52*t* that resides upstream of the tapered end 51*b* over the inner tube 51 such that the distal end of the inner tube extends distally a further distance than does the distal end of the second tube 52. The second tube 52 has a larger diameter than the inner tube 51.

The cannula 30 can snugly, slidably extend and reside over the second tube 52. The cannula 30 can be positioned upstream of the tapered end 51*b* on the dilation tube 50 prior to inserting the dilation tube in the body. In other embodiments, the cannula 30 can be separately inserted over the dilation tube 50 after the dilation tube 50 is inserted into the body. In any event, once the tapered end 51*b* reaches the facet joint J, the cannula 30 (also called a working tube) can be pushed down to the facet joint J so that the distal end 30*d* of the cannula 30 resides at the facet joint around the tapered end 51*b*. The dilation tube 50 (inner member 51 with tapered end 51*b* and second member 52, where used) can then be removed, leaving the cannula 30 in position.

Referring to FIGS. 7A-7D, a dilation tube 50 for the debridement procedure can include both a first inner tube 51 and a second tube 52 that slides over the inner tube 51. However, in other embodiments, the tubes 52, 51 can be provided as a single tube that be removed after the cannula 30 is in position. The dilation tube 50 can be semi-rigid or rigid and may comprise a molded polymeric body or bodies. The cannula 30 can be configured to slidably advance over the dilation tube 50.

Figure 7C:
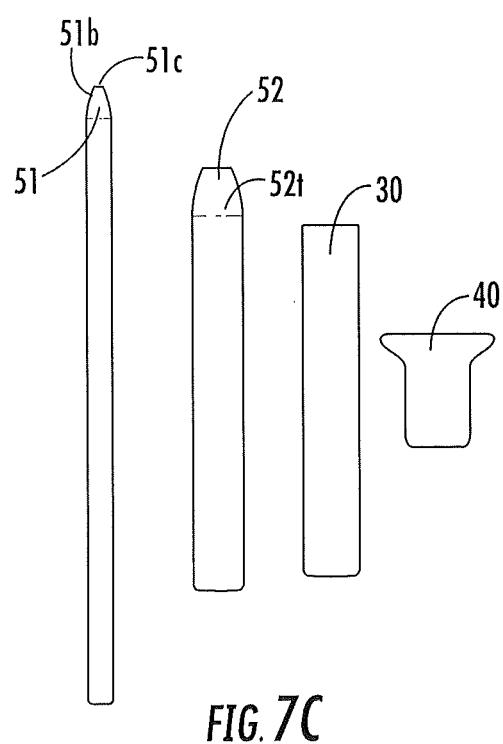
FIG. 7C is a top view of four disassembled cooperating tissue dilation components suitable for use in the debridement procedure.
Figure 7D:
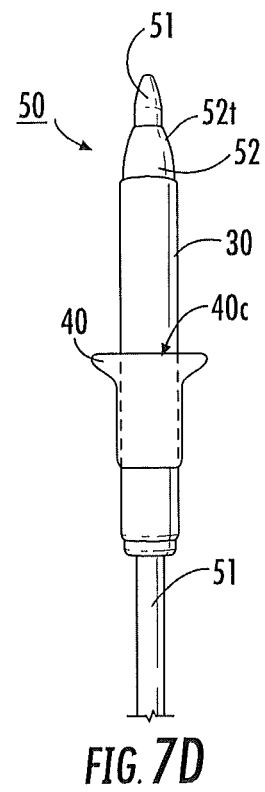
FIG. 7D is an assembled view of the components shown in FIG. 7C according to embodiments of the present invention.

FIGS. 7C and 7D illustrate that the stabilizer 40 can have an open channel 40*c* that allows the dilation tube 50 and/or the guide cannula 30 to extend therethrough.

The cannula 30 is typically rigid and formed of a material that may be compatible with autoclaving for sterilization. The cannula 30 can be metallic or other non-toxic and/or biocompatible material that is sufficiently rigid and that may be high-temperature (autoclave) heat-resistant.

Figure 8:
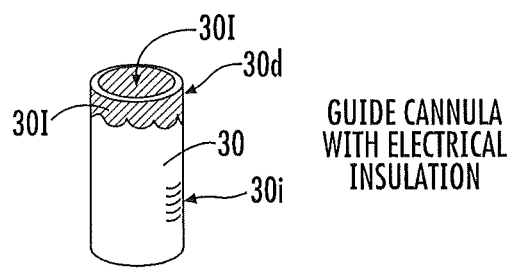
FIG. 8 is a schematic illustration of a cannula with electrical insulation material according to embodiments of the present invention.

Referring to FIG. 8, in some particular embodiments, the cannula 30 may comprise a stainless steel material with an inner surface having an electrically insulating material 30I. The electrical insulating material can be configured to inhibit arcing with the electro-cautery output, e.g., RF energy at the head 15, when the tool is configured to apply RF energy for the cauterization. The electrical insulating material 30I can be provided by an internal sleeve or coating or otherwise. The insulating material 30I may reside on only a distal end portion of the guide cannula 30 or over an entire inner surface of the cannula 30. The electrically insulating material 30I may optionally reside on the outer surface of the guide cannula 30, such as on the distal end thereof as shown.

As also shown in FIG. 8, the guide or working cannula 30 can have visible indicia of depth stop position 30*i* which may include a graduated scale or other visual information to facilitate positioning, which may also or alternatively be used to facilitate a desired position of the stabilizer 40 for a desired stop depth. As discussed above, the cannula 30 can have an electrically insulating material on at least an inner surface thereof. The cannula 30 can be metallic (and if so, preferably, but optionally, has the electrically insulating material 30I) or may be polymeric or other plastic material with sufficient rigidity to provide the guide path for the tool 10.

Figure 9A:
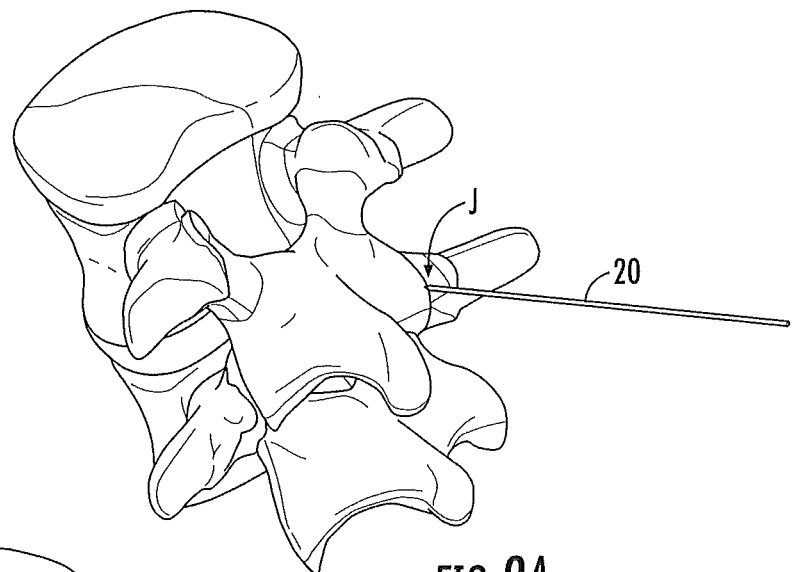
FIGS. 9A-9F are schematic illustrations of a sequence of operations that can be used to carry out a spinal debridement therapy according to embodiments of the present invention.
Figure 9B:
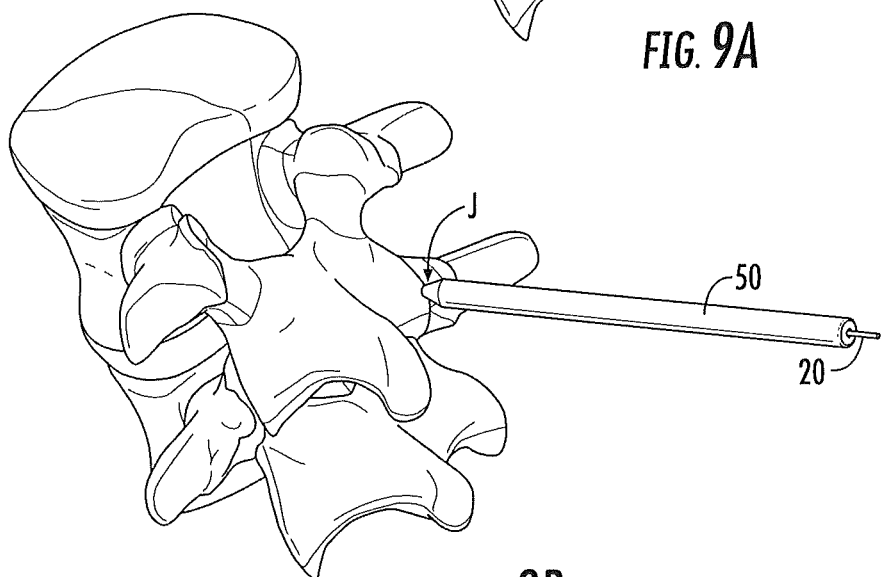
Figure 9C:
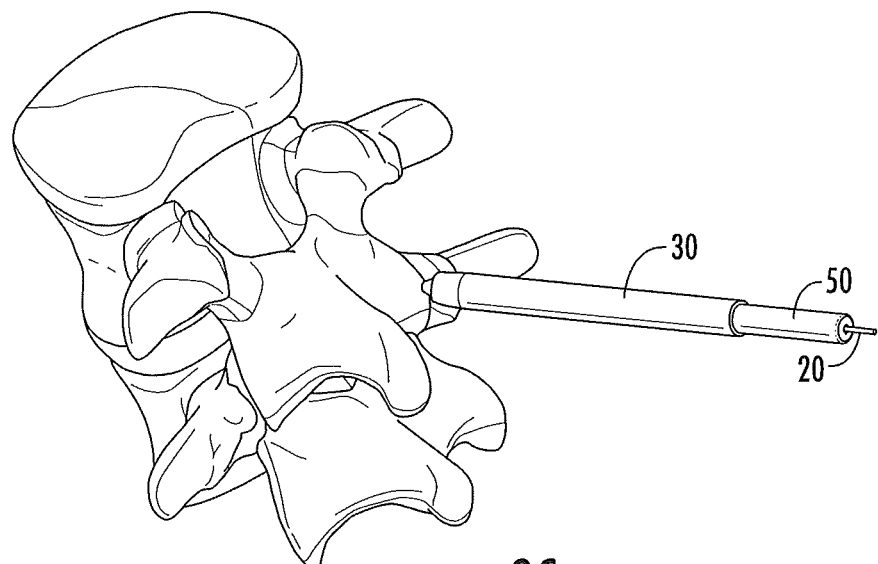
Figure 9D:
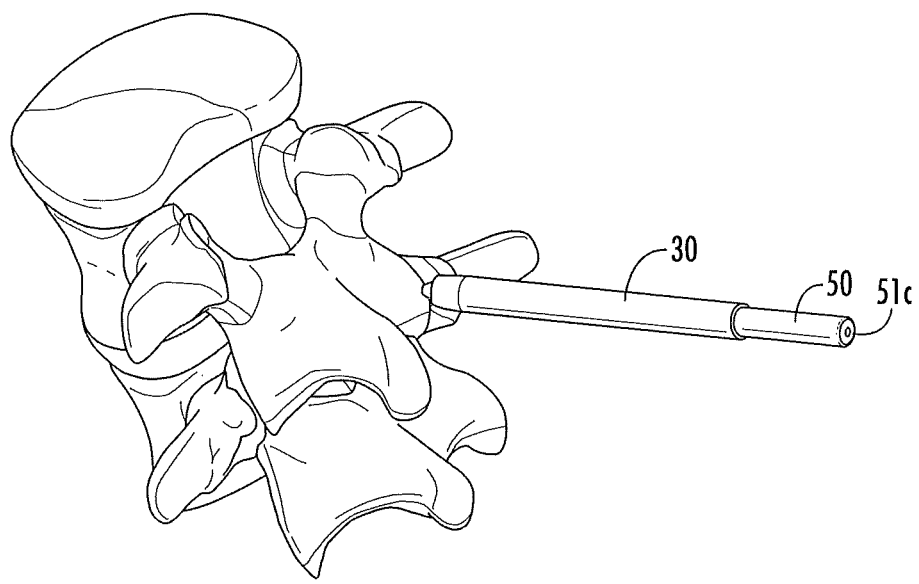
Figure 9E:
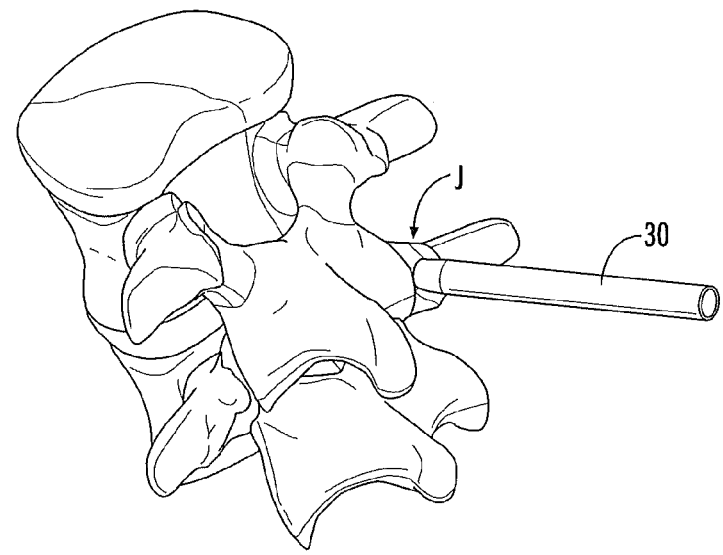
Figure 9F:
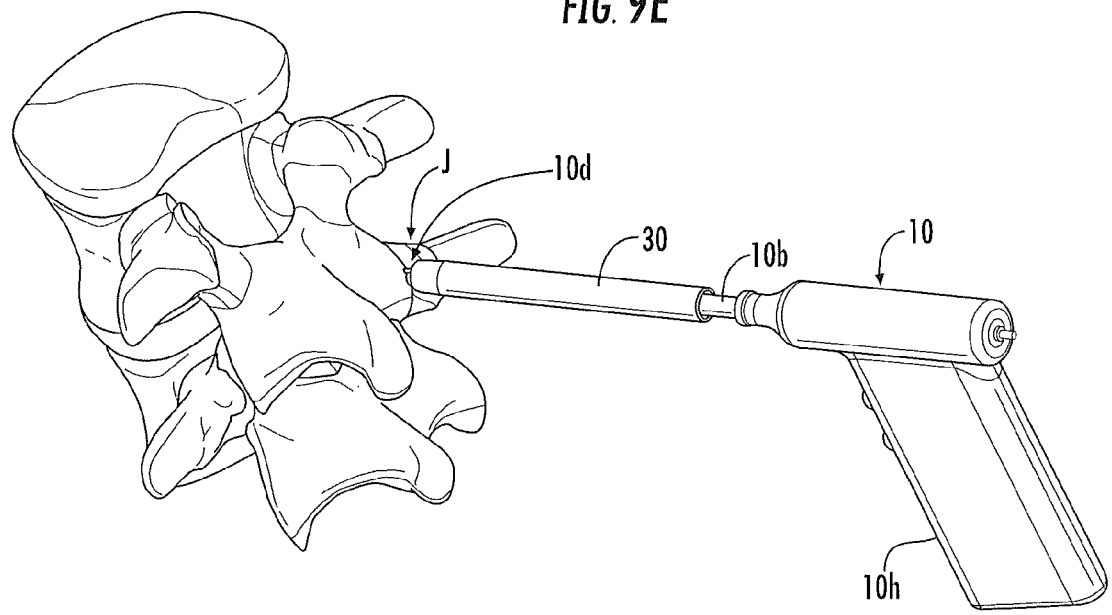

FIGS. 9A-9F illustrate an exemplary sequence of operations that can be used to carry out a spinal facet joint therapy to alleviate pain. The guide pin/guide wire 20 can be inserted into the patient. It is also noted that the guide pin/wire 20 is optional and that the dilation tube may be inserted without requiring the use of the guide wire/pin 20. Also, where used, the guidewire/pin 20 may extend through the cannula 30 rather than the barrel of the tool 10*b* and is not required to extend along a centerline of the device 10*b*, 30. For example, the cannula can have a guidewire channel 33 residing about a perimeter segment as shown in FIGS. 23C and 23E. FIG. 9F illustrates the barrel 10*b* of the tool 10 in the cannula 30 with the distal end extending out of the cannula at the treatment site J.

Prior to initiating active therapy with the tool 10 (e.g., activating the cautery and/or rotation of the head 15), confirmation of position can be carried out via fluoroscopy in AP and Lateral views to confirm three dimensional (3D) placement. The cannula 30 and/or the guide pin 20 can keep the distal end of the debrider tool 10*d* on the target spinal facet joint J.

Figure 9G:
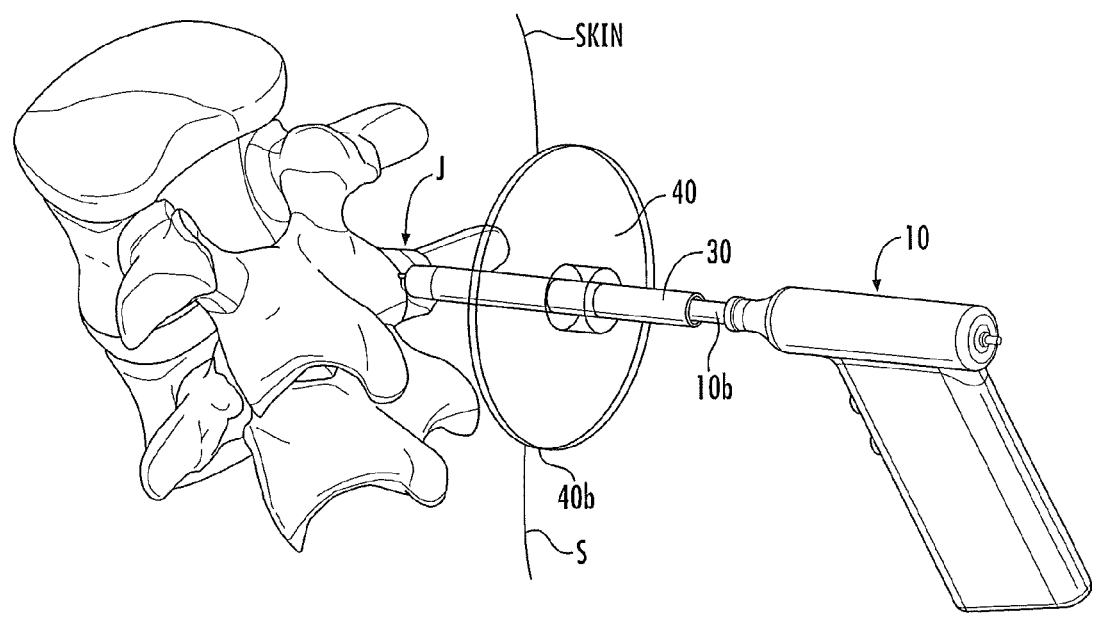
FIG. 9G is a schematic illustration of a therapy device in a working cannula similar to FIG. 9F but also cooperating with an external stabilizer according to embodiments of the present invention.

FIG. 9G illustrates the use of the stabilizer 40. The stabilizer 40 (when used) can be positioned prior to, during or after insertion of the guidewire/pin 20 (where used), the dilation tube 50 and/or the cannula 30.

The tool head 15 can be rotated to denude tissue until bone at the target spinal facet joint is reached. In preferred embodiments, the rotation of the head 15 can be automatic using a motor M (FIG. 10A, 10B, 14, 21A-C, 22A-C) with a drive shaft 18 (FIG. 10A) connected to the therapy tool head 15. However, in some embodiments, the denudement head 15 can be manually rotated. The therapy tool head 15 is also configured to cauterize the soft tissue during and/or after the denuding.

In some embodiments, the tool 10 can have an elongate barrel 10*b* with a length sufficient to reach the target intrabody spinal facet site. The length of the barrel 10*b* can be between about 100 mm to about 150 mm.

The cannula 30 can have a diameter that is slightly larger than the outer diameter of the tool barrel 10*b*, e.g., between about 0.1 mm to about 1 mm to allow snug sliding entry of the tool 10. The tool 10 can have various form factors. For example, the tool 10 can have a hand-held linear (e.g, pen-like) shape with the barrel 10*b* forming the handpiece/grip 10*h* (FIG. 21A, 24B) or the tool can have a pistol shape with a barrel 10*b* and a downwardly extending handgrip 10*h* (FIG. 9F, 21B, 21C, 24A). The barrel 10*b* may rotate or be static. The barrel 10*b* can form part of the drive shaft 18 or substantially or totally encase the drive shaft 18 of the rotating head 15.

During use, the proper "stop" for a treatment and/or denuding action can be confirmed by a manual tactile feel since the debrider tool 10 can be made to remove the soft capsular tissue and superficial lining of the joint J but when the bone is reached by the head 15, the tool 10 will not advance or there will be increased resistance and the surgeon can "feel" in a tactile feedback manner that he or she is up against the hard surface of the bone. However, as noted herein, sensors can be used to provide feedback/electronic control.

The denuding of target soft tissue with the tool 10 can have a duration (with the active rotation of the debridement tool head) that is between about 30 seconds to about 3 minutes long, typically between about 30 seconds to about 2 minutes, on average.

FIG. 10A illustrates that the tool 10 can include a sensor 60*s* that provides visual and/or audible output to a user that the soft tissue has been removed and the head 15 has reached the bone at the spinal facet joint J. The sensor 60*s* can be in communication with the drive shaft 18 that is connected to the motor M or with the head 15 directly or indirectly. The sensor 60*s* can be a torque sensor, a strain gage, or an optical sensor (for detecting a lower number of revolutions of the driveshaft over time). The tool 10 can include a processor or control circuit 50 that monitors the sensor 60*s* and provides the output to a display, LED, speaker or other output device. When increased torque, strain or a slower speed is indicated by the sensor 60*s*, the visual and/or audible alert 60*a* can be generated by the control circuit 50 to the output device 60. Alternatively, the visual/audible alert 60*a* can just be generated to supplement a surgeon's tactile (manual) control of the tool 10 as an aid to confirm that the desired tissue has been denuded (and/or as a training tool to teach a surgeon the tactile response associated with the denudement "stop").

The tool 10 can be configured to continuously rotate the head 15 during both cauterization and subsequent (light) tissue scraping/cleansing upon contact with bone at the facet joint J. In some embodiments, the tool 10 can be configured to discontinuously rotate the head 15 and/or interleave the cauterization with the rotation.

Once the soft tissue is denuded, the tool head 15 can be rotated with sufficient force and time to contact the outer surface of the bone under the denuded tissue for a desired short time, e.g., between about 10 seconds to about 2 minutes, more typically between about 10 seconds to about 60 seconds, to cleanse an exposed outer surface of the bone thereat substantially without removing bone. The short tissue cleansing/scraping time, post-cauterization (e.g., post-denuding), can be controlled with an auto-shutoff for the tool rotation and can be timed based on user or electronic (auto) shut off of the cautery/burn or based on sensor feedback of contact with bone.

The tool 10 can be rotated with the same rotational speed for the bone surface cleansing relative to the denuding action or with a different rotational speed and/or force for the bone surface cleansing relative to the denuding action. In some embodiments, the tool 10 has a first defined rotational speed range for the denuding and a different defined rotational speed range for the cleansing. The transition from denuding (with or without cauterizing) to cleansing can be automatic or manual. If automatic, a sensor can trigger the transition to a different speed and/or to terminate the power to stop the cauterizing action. If manual, a user interface (UI) via a control such as a switch or a voice prompt to a control circuit can direct the change in operation, e.g., slow rotation and stop cautery/burn.

In some embodiments, the tool 10 can be configured to apply the cauterization without rotation of the head 15 then cleanse/tissue scrape with the rotation of the head 15. This may be particularly suitable for laser, ultrasound or cryo-ablation configurations.

In some particular embodiments, the different speeds can be selectively applied by the user via at least one user input 61, such as denude and cleanse mode control inputs 62, 63 on the tool 10 that are in communication with the control circuit 50 and motor M. The inputs 61 may be a single physical input comprising one or more knobs, buttons, triggers, or GUI inputs on a miniature touch screen display onboard or in communication with the tool 10. The UI can comprise voice-based inputs/commands, e.g., "START DENUDE, START/STOP CAUTERIZE, START/STOP SCRAPE" and the like.

The different speeds for the cleanse and denude modes may be automatically applied by the control circuit 50 based on input from the sensor 60*s*, where used. In some embodiments, the cleanse mode has a 10-100% faster rotation speed than the denude mode while in other embodiments, the cleanse mode has a slower rotation speed (e.g., 10-100% slower) than the denude mode.

The speed of the therapy delivery tool head 15 (e.g., a tissue scraper and cautery head) can be relatively low to avoid cutting into the bone. Most orthopedic burrs will operate up to 60,000 rpm which can be hard to control and can dig into the bone. Thus, lower rotational speeds are desired for both the denuding and cleanse modes or action. The objective is to sweep the tissue off the bone and not drill into the bone during the cleanse mode. Thus, in some embodiments, for both denuding and cleansing of the bone, a speed of below about 5000 rpm may be appropriate, typically between about 10 rpm to about 5000 rpm, and more typically between about 10-1000 rpm. The speed may be different for the cauterizing and the tissue cleansing/scraping. In some embodiments, the speed is between about 10 to about 5000, including about 125 rpm, about 150 rpm, about 200 rpm, about 250 rpm, about 300 rpm, about 350 rpm, about 400 rpm, about 450 rpm, about 500 rpm, about 550 rpm, about 600 rpm, about 650 rpm, about 700 rpm, about 750 rpm, about 800 rpm, about 850 rpm, about 900 rpm, about 950 rpm, about 1000 rpm, about 1500 rpm, about 2000 rpm, about 2500 rpm, about 3000 rpm, about 3500 rpm, about 4000 rpm, about 4500 rpm and about 5000 rpm.

In some embodiments, the speed is low speed for one or both the denuding (with or without cauterizing) and the cleansing. The term "low speed" means between about 10 rpm to about 100 rpm, including about 10 rpm, about 15 rpm, about 20 rpm, about 30 rpm, about 40 rpm, about 50 rpm, about 60 rpm, about 70 rpm, about 80 rpm, about 90 rpm and about 100 rpm.

While not necessary, the tool 10 can have a cleanse run mode that rotates the therapy delivery tool head 15 at a slower speed than a denuding speed (if rotated during denuding). In some embodiments, the tool 10 can have a substantially constant rpm with a controlled maximum output of maximum operational capacity at full speed of between about 10 rpm to about 5000 rpm, typically between about 10 and 200 rpm, and more typically with a maximum rotational speed of between about 10 rpm to about 100 rpm.

FIG. 10B illustrates that the tool 10 can include a speed limiter control 77 to insure that the maximal rotational speed allowed is between about 10-5000 rpm. The use of properly sized gears/clutches, speed governors, electronic cut off sensors or other mechanisms can be used to control the maximal speed.

The tool 10 can be configured to have a maximum speed (at full speed) that is between about 10 to about 5000 rpm, typically between about 10-1000 rpm such as between about 10-500 rpm or between about 10-100 rpm including about 40 rpm.

In some embodiments, a viewing scope can be placed in the cannula 30 or in an adjacent cannula or port (not shown) to allow real time viewing of the spinal joint J during the therapy.

The denuded soft capsular tissue can be suctioned via vacuum or otherwise removed by the spinal facet therapy (e.g., debrider) tool 10 or with another tool. In some embodiments, the tool 10 can be connected to an irrigation source 171 and/or a vacuum/suction source 172 as shown in FIG. 10B. The tool 10 can comprise an irrigation channel 71 and a suction/vacuum channel 72 with respective ports 71p, 72p on the distal end of the tool 10d (FIG. 25C). A single channel can be used for both irrigation and suction where both functions are provided. FIG. 26 illustrates an example of a two channel configuration, e.g., the irrigation and vacuum/suction channels 71, 72.

The surgical site J can be flushed out with saline or other suitable cleansing liquid and suctioned and removed. The flushing of the site can be carried out using the debrider tool 10 or without the debrider tool 10. If the latter, the tool barrel 10b can reside in the cannula 30 during the irrigation and/or suction. The cannula 30 may remain in place during the flushing or removed before this action. The stabilizer 40, where used, can be removed before or after the guide cannula 30. The therapy delivery tool 10 can be removed before, after or with removing the cannula 30. The guide pin 20 can be removed before, after or with the tool 10 and/or cannula 30 (or even earlier if not needed according to some embodiments, for example).

This procedure can be repeated for each joint selected for treatment. Typically, between two and six joints J can be treated at one therapy session.

In some embodiments, to save time, all of the guide pins 20 on one side for each joint J can be placed before any incisions and/or before debriding at any level. Sterile surgical tape such as 3M™ Steri-Strips™ and/or a small suture (or surgical glue) can be placed to close a respective incision wound once the therapy is complete.

Post-pin placement, the entire spinal facet treatment procedure for one joint J can take between five to fifteen minutes. The procedure can be an outpatient procedure and the patient can typically walk the same day with recovery over a week to let the surgical sites heal.

Figure 11A:
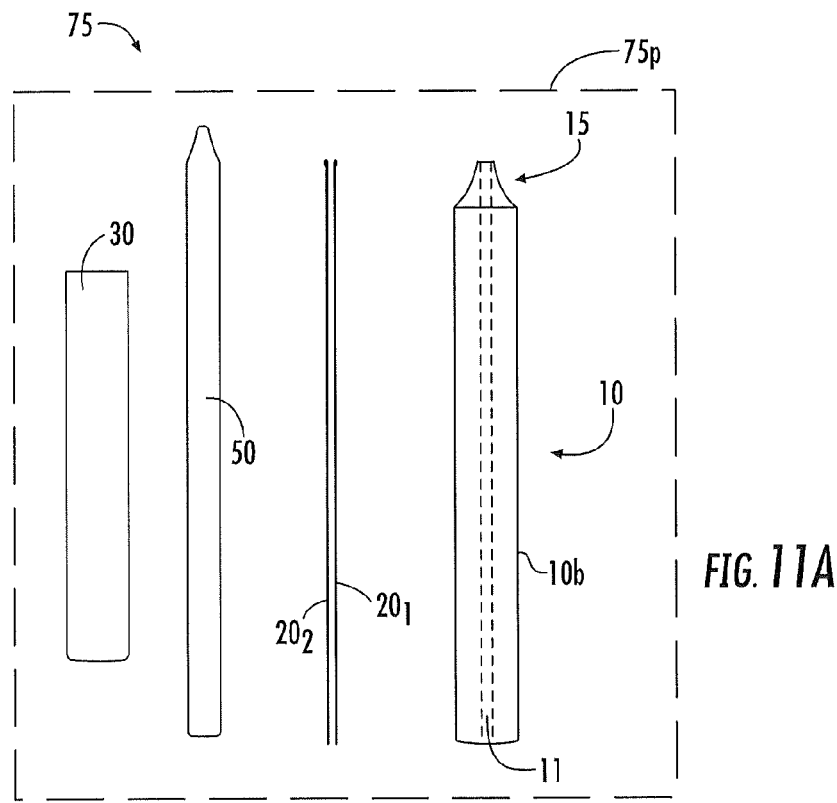
FIG. 11A is a schematic illustration of a kit for spinal facet debridement surgical procedures to alleviate pain according to embodiments of the present invention.
Figure 11B:
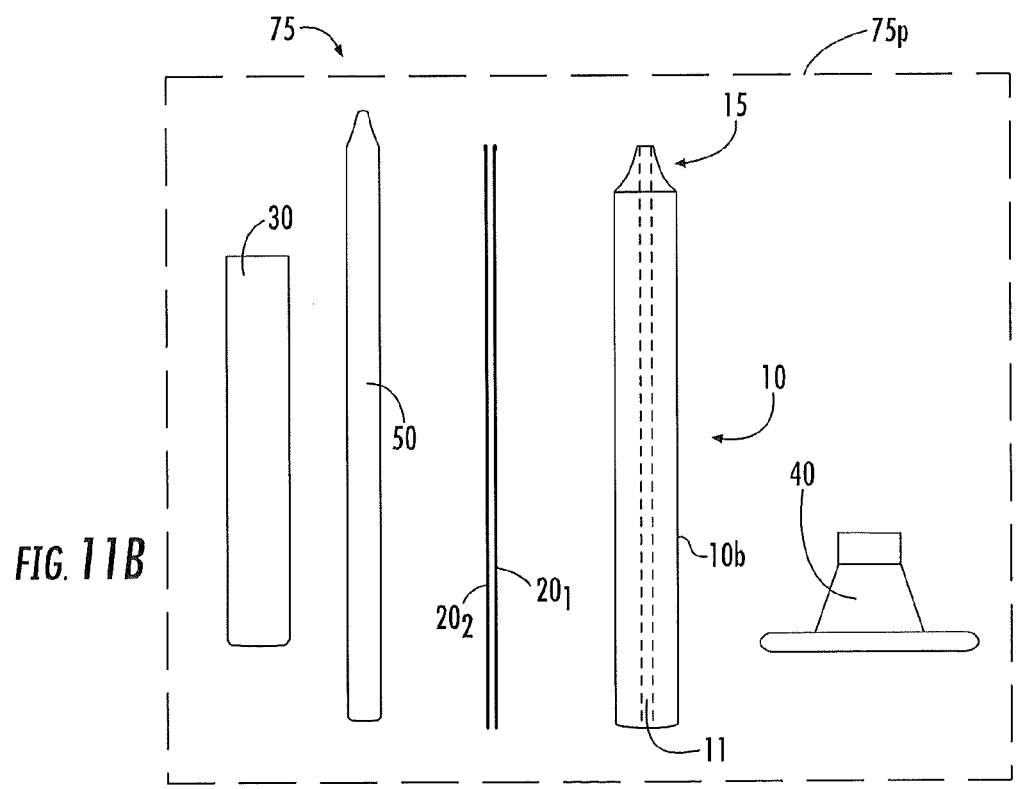
FIG. 11B is a schematic illustration of another embodiment of a kit for spinal facet debridement surgical procedures to alleviate pain according to embodiments of the present invention.

FIGS. 11A and 11B illustrate examples of a spinal facet debridement surgical tool kit 75. As shown, the kit 75 can include a package 75p with sterile components that facilitate the surgery. The kit 75 can include a debrider tool 10 (which can be the entire therapy delivery tool 10 or a consumable, single use disposable or multi-use barrel 10b), optionally a plurality of guide pins $20_1$, $20_2$ (shown as two, but one or more than two can be provided, or the pins can be provided separately outside the kit), a dilation tube 50 and at least one cannula 30 (or working tube). FIG. 11B illustrates that the kit 75 may include the stabilizer 40. While shown as kits with all the noted components for facilitating ease of surgical preparation, the components may be provided as separate units.

The cannula 30 can be provided pre-attached to the dilation tube 50 or provided as a separate component. For bilateral and/or multi-level procedures, more than one cannula 30 and, where used, more than one stabilizer 40, may be included, and if so, may be labeled for right and left sides and/or for indicating spinal treatment levels. The dilation tube 50 can be a single tube or may include multiple components as shown in FIG. 11A, for example. The guide pins 20 can be provided in a common size or different sizes, typically with a diameter that is between about 0.75-1.25 mm, more typically about 1.0 mm.

Figure 12:
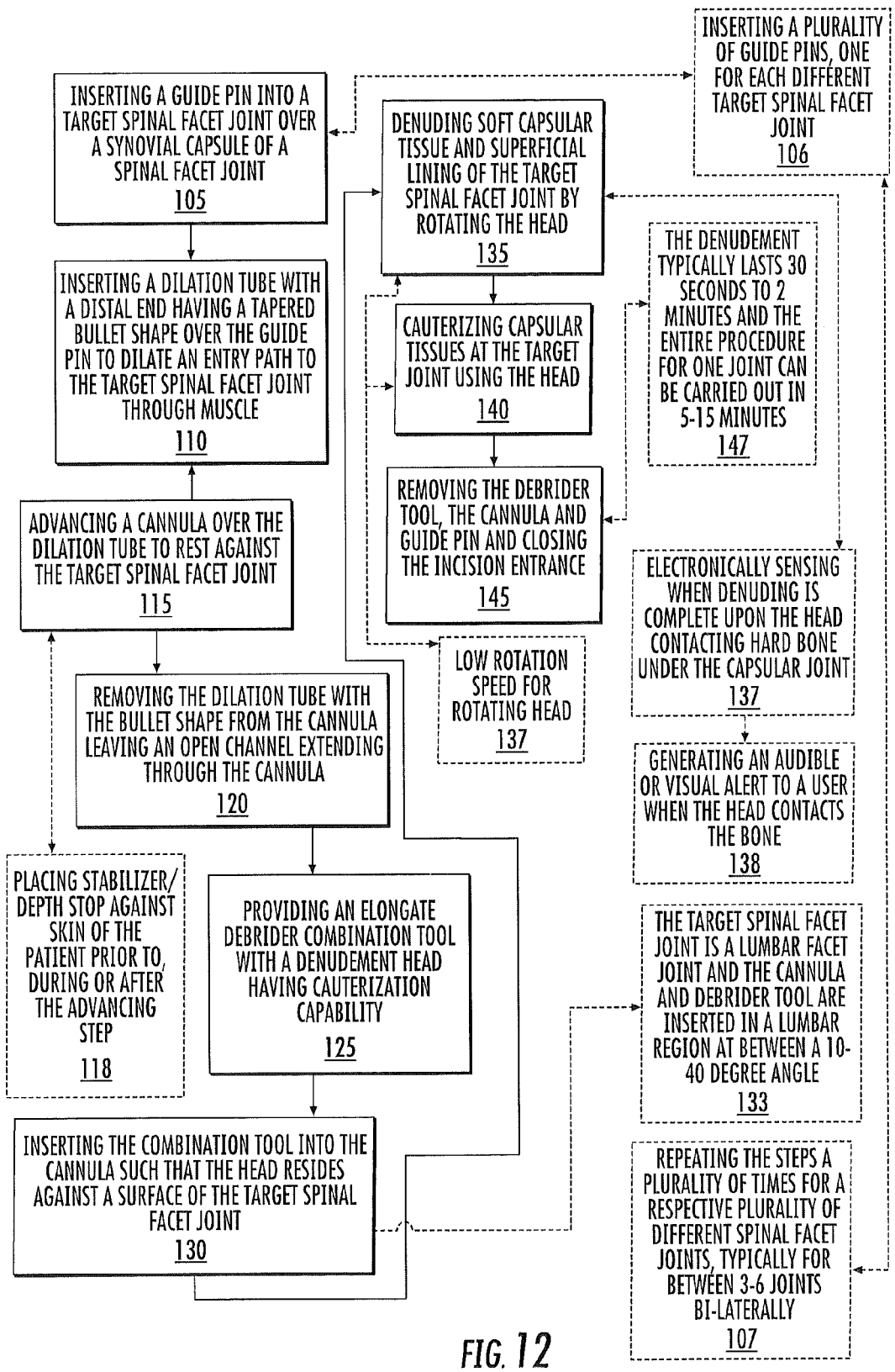
FIG. 12 is a flow chart of exemplary operations that can be used to perform a spinal facet therapy to alleviate pain according to embodiments of the present invention.

FIG. 12 is a flow chart of exemplary actions that can be used to carry out a spinal facet treatment to alleviate pain associated with arthritis. A guidewire/pin is typically inserted into a target spinal facet joint over a synovial capsule of a spinal facet joint (block 105). A dilation tube with a distal end having a tapered bullet shape is inserted over the guide pin to dilate an entry path to the target spinal facet joint through muscle (block 110). A cannula is slidably advanced over the dilation tube to rest against the target spinal facet joint (block 115). The dilation tube with the bullet shape is removed, leaving the cannula with an open channel extending therethrough in position (block 120). An elongate debridement tool with a denudement head having cauterization capability ("combination tool") is provided (block 125). The combination tool is inserted into the cannula such that the head resides against a surface of a target spinal facet joint (block 130). Soft capsular tissue and a superficial lining of the target spinal facet joint are denuded by rotating the head (block 135). Tissue at the target joint is cauterized using the head (block 140).

The treated joint can be flushed and suctioned. The therapy delivery (e.g., debrider) tool, cannula and guide pin can be removed and the incision entrance closed (block 145).

In some embodiments, an external stabilizer can be placed against the skin of the patient prior to, during or after the cannula is advanced (block 118).

In some embodiments, the denuding and/or cauterizing can be carried out using a low rotation speed for the rotatable tool head (block 137).

In some embodiments, a plurality of guide pins can be inserted, one for each different target spinal facet joints (block 106). Steps 110, 115, 120, 130, 135, 140 and 145 can be repeated at each respective different spinal facet joint, typically between 2-6 joints, including 2 joints, 3 joints, 4 joints, 5 joints and 6 joints (block 107). Usually two or three levels, bilaterally, are debrided during a single surgical session.

The denudement typically lasts between about 10 seconds to 3 minutes (average), more typically between about 30 seconds to 2 minutes (average), and the entire procedure (post pin placement or including pin placement) for one joint can be carried out in about 5-15 minutes (typically bilaterally per joint) (block 147).

The head 10 can be configured to denude and cauterize soft tissue at the target spinal facet joint either serially (e.g., intermittently or interleaved) and/or concurrently. The tool 10 can allow a user to select when to cauterize or it can be configured to automatically cauterize during the entire denuding action, during a portion of the denuding action, or after a denuding action.

In some embodiments, the method can include electronically sensing when denuding is complete upon contact with bone under the capsular joint (block 137). The method may optionally include electronically generating an audible or visual alert to a user when the head contacts the bone and/or when the denuding of soft tissue is complete (block 138).

In some embodiments, the target spinal facet joint is a lumbar facet joint and the cannula 30 and debridement tool 10 can be inserted in a lumbar region at between a 10 to about a 40 degree angle, typically between about 20-30 degrees for this region (block 133). Other levels, e.g., cervical and thoracic debridement may be at other angles typically between about 0 to about 10 degrees.

It will be appreciated that angulation of the tool 10 can change depending on scoliosis, etc. Typically, the lumbar region is between about 10 to about 40 degrees as noted above. However, the angulation is appropriate so as to be perpendicular to the target spinal facet joint surface, which is usually about 10 to about 40 degrees laterally in the lumbar region and between about 0 to about 10 degrees laterally in the thoracic and cervical regions.

Figure 13A:
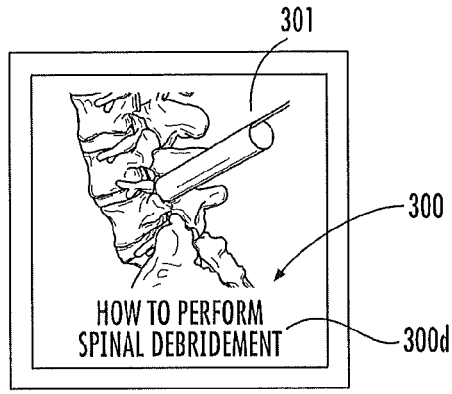
FIG. 13A is a schematic illustration of electronic instructional media for a spinal facet therapy procedure to alleviate pain according to embodiments of the present invention.
Figure 13B:
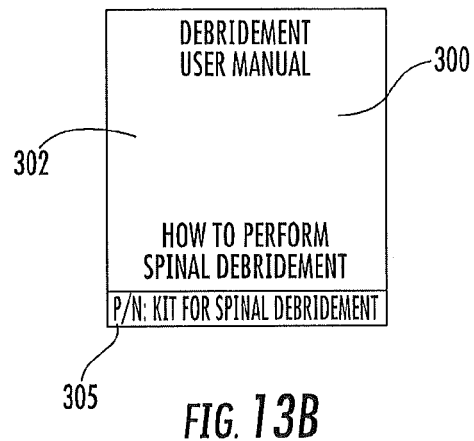
FIG. 13B is a schematic illustration of a user manual for use of the debridement tool for a spinal facet joint according to embodiments of the present invention.

FIGS. 13A and 13B illustrate that instructional media 300 can be provided either electronically (FIG. 13A) and/or in paper form (FIG. 13B) that facilitates proper use and/or training of surgeons to carry out a spinal debridement procedure for spinal arthritis pain using a spinal facet debridement tool 10 that both denudes and cauterizes synovial capsule tissue. The media can include a suitably descriptive title and/or label identifying the content as instructions/training material for a spinal facet therapy to alleviate pain. The media 300 can include a video or electronic instructional manual 30I that can be shown on a display 300*d* showing a sequence of surgical steps, an actual procedure or both, to carry out a spinal debridement procedure using a spin. The instructional media can be provided via the Internet such as at a hosted internet portal/site, via an APP for a smart phone, computer, electronic notebook or tablet and the like, typically via the use of an icon with defined functionality as is known to those of skill in the art.

The paper media 302 can include a paper user manual or booklet such as an instructional manual showing a sequence of surgical steps to carry out a spinal debridement procedure and/or proper operation of a spinal facet debridement tool that both denudes and cauterizes synovial capsule tissue.

A part number 305 of the kit 75 with ordering information can be included in the instructional media 301, 302.

Figure 14:
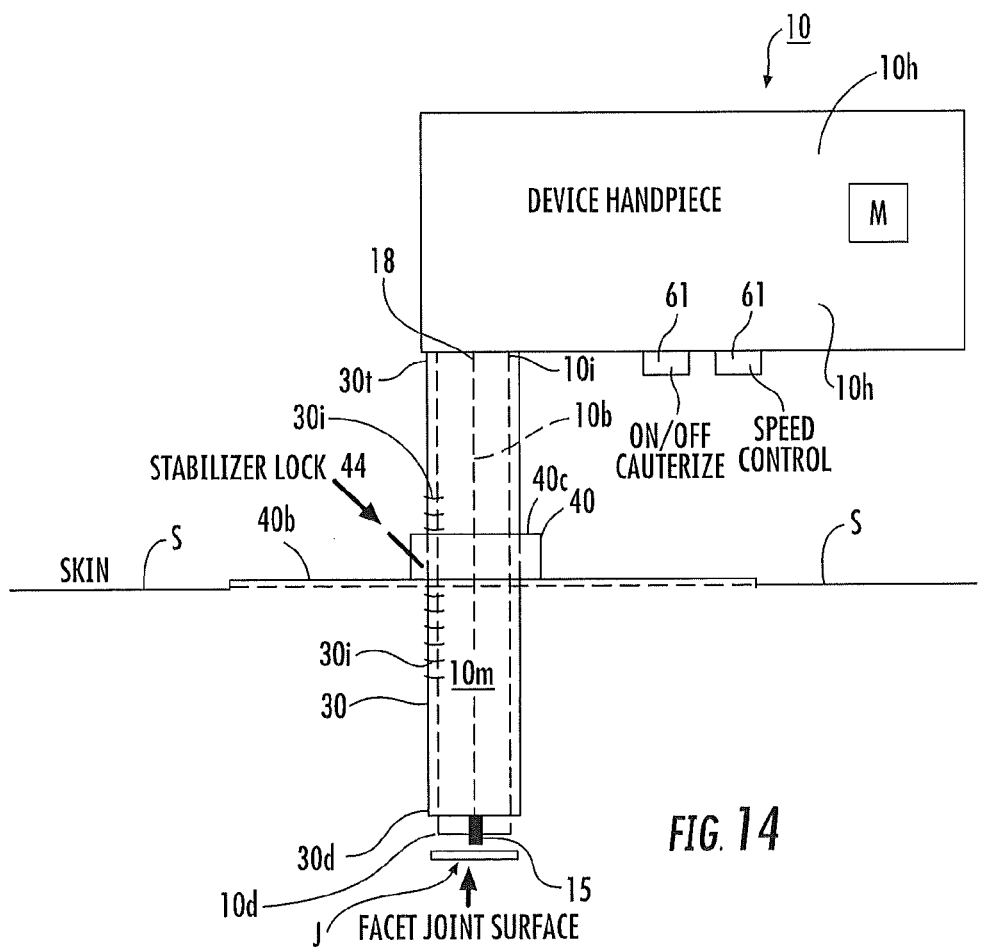
FIG. 14 is a schematic illustration of exemplary positions of cooperating components of a spinal facet therapy delivery system according to embodiments of the present invention.

As shown in FIG. 14, the stabilizer 40, where used, can have a through-channel 40*c* that is configured so that the tool barrel 10*b* extends through this channel 40*c* for a defined intrabody depth to the therapy site J. The stabilizer 40 can releasably, slidably engage the guide cannula 30. The stabilizer 40 can be configured to lock 44 against the outer surface of the cannula 30. The locking engagement 44 can be provided using a physical lock member (e.g., a clamp or other suitable lock) or a locking configuration, e.g., frictional engagement or other locking configuration between the cannula 30 and the tool barrel 10*b*. The stabilizer 40 and cannula 30 engagement can be through any suitable physical engagement that allows the stabilizer to lock against the cannula 30 directly or indirectly.

The therapy device 10 can be configured such that when the elongate barrel 10*b* is inserted fully through the guide cannula 30 in an operative configuration, the head 15 and/or distal end of the therapy device 10*d* extends beyond the front or distal end 30*d* of the cannula 30 only by between about 2 mm to about 7 mm, such as about 2 mm, about 2.5 mm, about 3 mm, about 3.5 mm, about 4 mm, about 4.5 mm, about 5 mm, about 5.5 mm, about 6 mm, about 6.5 mm or about 7 mm. Thus, the stabilizer 40 locks the cannula 30 in a longitudinal position. The stabilized/locked position of the cannula 30 relative to the skin of the patient S keeps the distal end 10*d* of the barrel 10*b* and/or head 15 from moving deeper into the body.

The top of the guide cannula 30*t* and tool interface 10*i* keeps the tool barrel 10*b* from moving relative to the cannula 30. The cannula and tool interface 10*i* can be provided in any suitable configuration. In the example illustrated, the interface 10*i* is shown based on the shape of the tool and top of the cannula 30*t*, e.g., through abutting contact to provide a physical interference/stop.

The stabilizer 40 may optionally provide some structural support for the guide cannula 30 and/or tool 10 at the entry site. As noted above, the stabilizer 40 can have a bottom 40*b* that has a greater width/surface area than the primary body 40*b*. The width of the bottom 40*b* can be larger than the width of the cannula 30 by between two-ten times. Typically, the stabilizer bottom 40*b* has a width that is between about 1-6 inches, more typically between about 3 to about 5 inches. The stabilizer bottom 40*b* can be thin, typically between about 1-10 mm, more typically between about 2 to about 4 mm. The bottom 40*b* can be semi-rigid or rigid. The bottom 40*b* can be configured to conformably reside against the skin of the patient.

FIG. 14 illustrates that the tool barrel 10*b* can have visual indicia of depth markings 10*m* which may be in a graduated scale in defined increments positioned along the length dimension. The guide cannula 30 can also or alternatively have the visual depth markings 30*i*, typically in an incremented, graduated scale. The scale can be in microns or millimeters or other defined increments of length position. In some embodiments, the depth indicia marking 10*m* and/or 30*i* may be color-coded to reflect shorter versus longer depths or having depth indicia for visual correlation of depths for different treatment levels of the spine.

The longitudinal position of the guide cannula 30 relative to the stabilizer 40 can be adjustable to allow a clinician to adjust for a specific patient and/or target joint to thereby adjust the intrabody depth of the therapy tool delivery head 15 once inserted into the guide cannula 30 that is locked into its desired position by the stabilizer 40.

Figure 15A:
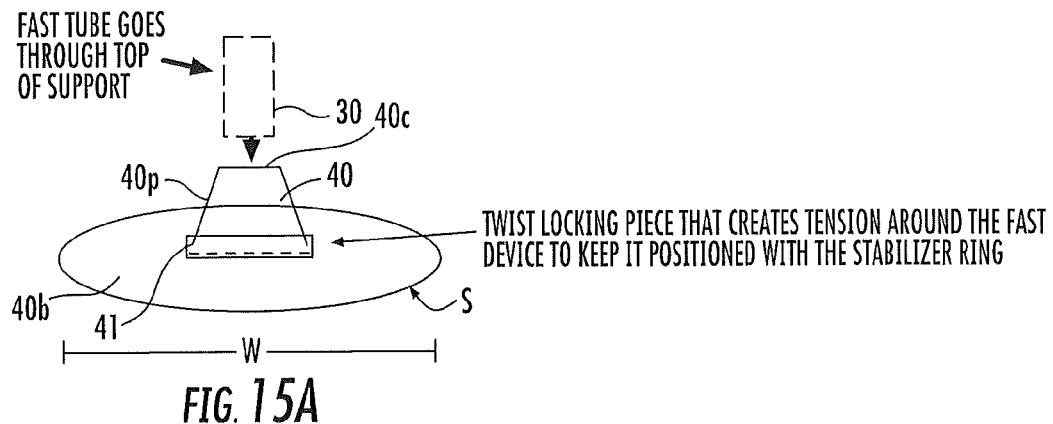
FIGS. 15A-15C are schematic illustrations of an example of a skin-mounted device according to embodiments of the present invention.
Figures 15B, 15C:
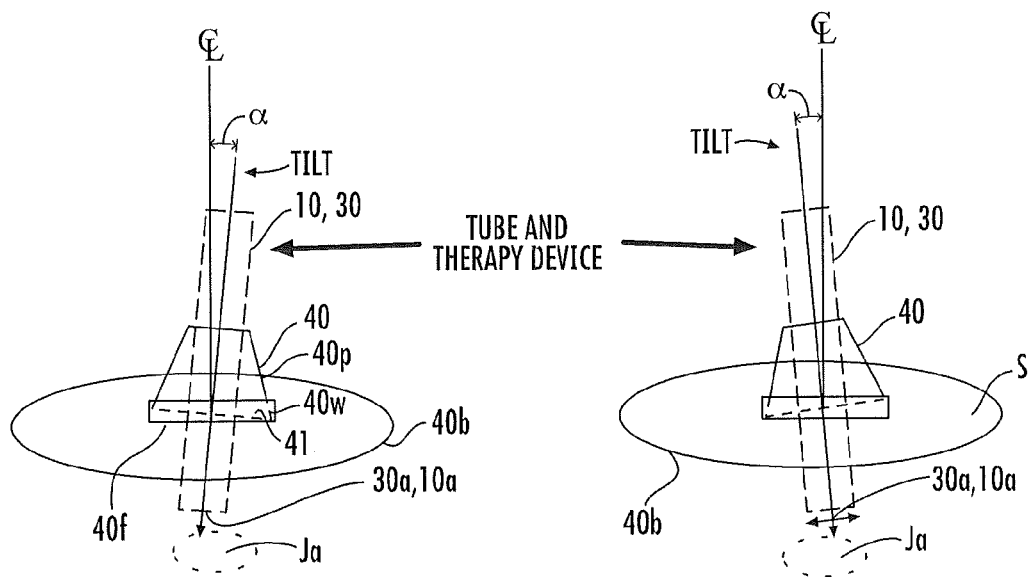

Referring to FIGS. 15A-15C, the stabilizer 40 can be configured to hold the cannula 30 and/or tool 10 (e.g., hold the tool directly with or without the cannula 30) in a manner that allows the tool barrel 10*b* to tilt T a few degrees front to back and side to side. Where used, the cannula 30 may also be configured to tilt. The tilt T is typically between about 2 to about 10 degrees, and more typically between about 3-6 degrees, such as about 3 degrees, about 4 degrees, about 5 degrees and about 6 degrees, from an axially extending centerline C/L of a static component (e.g., base and/or skin contact surface) of the stabilizer 40 so as to allow the distal end of the tool head 15 to contact a greater surface area Ja of the facet joint J while utilizing a smaller diameter device. That is, in some embodiments, compared to a straight and non-tiltable configuration, the size of the treated area Ja can be greater by between about 10% to about 100%. The tilt T can be in all directions, e.g., about 360 degrees when the cannula 30 has a circular cavity.

The handle of the tool 10*h* can include at least one user input member 61, such as an "on/off" cautery control and/or a speed adjustment control. The inputs may be and suitable user interface including one or more of knobs, buttons, triggers, rocker switches, and/or GUI inputs on a miniature touch screen display.

The stabilizer 40 can have a plurality of cooperating components that cooperate to hold the therapy device 10 and/or guide cannula 30 and prevent the therapy head 15 from advancing too deep into the body.

FIGS. 15A-15C illustrate an exemplary two-piece configuration of the stabilizer 40. The device 40 can have a base 41 that holds the primary body 40*p*. The base 41 can be structurally rigid or semi-rigid to sit against the skin S to stabilize the tool 10 from advancing too deep into the body. The base 41 can be configured to create a tension or compression around the guide cannula 30 to securely hold the cannula 30 at a desired longitudinal position with respect to the stabilizer 40. The primary body 40*p* can twist, frictionally engage or otherwise lock against the base 41. The base 41 can be attached to a wider bottom 40*b*.

The stabilizer body 40*p* can be configured to attach to the base 41 while allowing the body 40*p* to tilt T a few degrees in all directions from an axially extending centerline C/L of the base 41 so as to allow the distal end of the tube 30*d* and the tool head 15 to contact a greater surface area of the facet joint while utilizing a smaller diameter device. That is, as shown in FIGS. 15B and 15C, the tool head 15 can have a surface area 15*a* and/or the cross-sectional area of the channel 30*c* can have an area 30*a*, both of which are smaller than the treated (cauterized and tissue scraped) area of the joint Ja using the tool head 15 because of the tilt T allowed by the stabilizer 40. The treated area includes a treatment area corresponding to the area 10*a*, 30*a* of the cavity size of the cannula 30 and/or tool distal end 10*d* as well as the additional circumferentially extending area allowed by the tilt T. The stabilizer 40 can have a "joy stick" configuration to provide the desired tilt T.

The base and primary body 41, 40*p* may comprise a molded polymeric body. The bottom 40*b* can be circular with a diameter that is about 3-5 inches, with any suitable thickness. In some embodiments, the base 41 has an upper extending wall 40*w* that faces the primary body 40*p* and or the floor 40*f* forming the bottom surface 40*b*, each of which may be relatively thin, e.g., between about 2-4 mm. The stabilizer 40 may comprise other materials.

The stabilizer 40 can have other configurations. In addition, the tilt T can be provided by other designs. For example, the stabilizer 40 can comprise elastic components that extend between the barrel 10*b* and the stabilizer body 40*p*, e.g., one or more of a resilient plug of material, O-ring, a spring or springs and the like or a locking pin and slot arrangement.

Figure 16A:
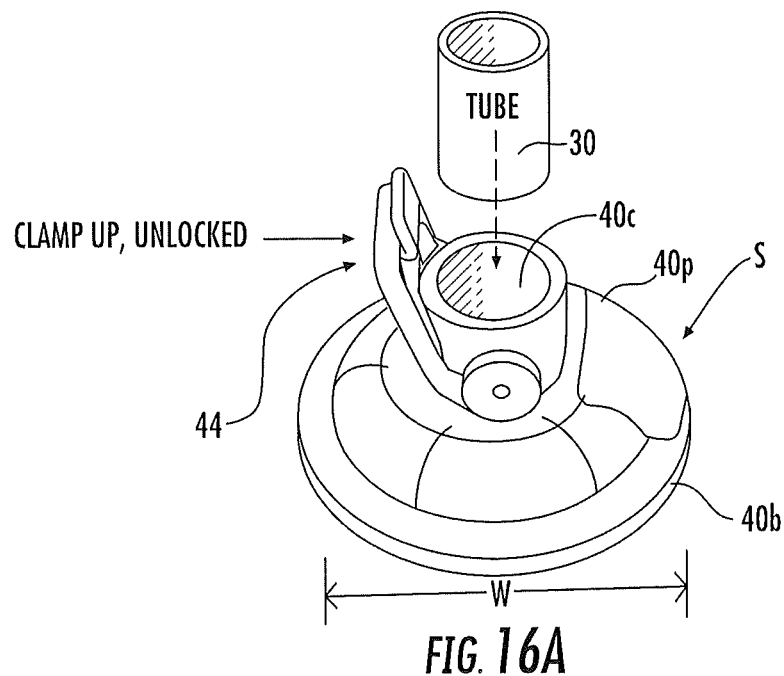
FIGS. 16A and 16B are enlarged side perspective views of another stabilizer configuration illustrating a pre-lock and post-lock configuration, respectively, according to embodiments of the present invention.
Figure 16B:
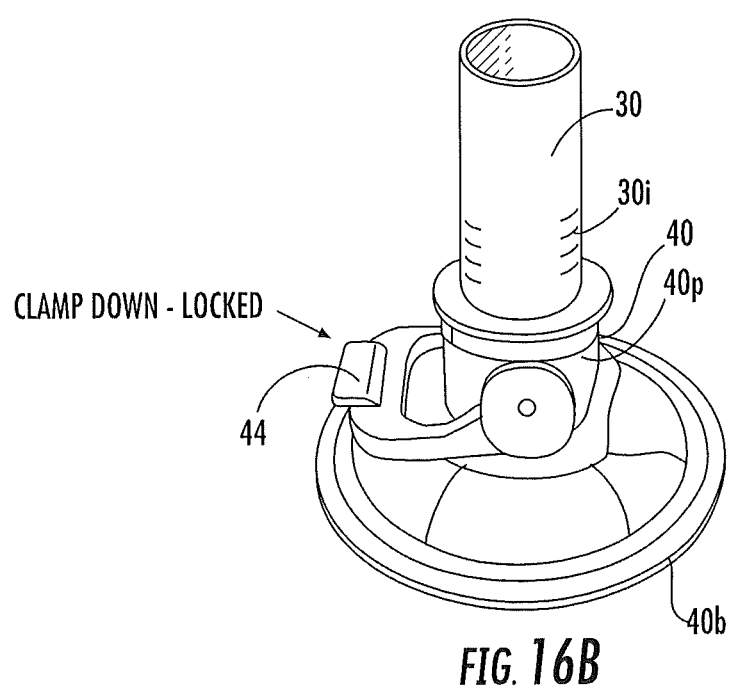

FIGS. 16A and 16B illustrate another embodiment of a stabilizer 40. As shown, the stabilizer 40 includes a lock 44 that can be translated (e.g., pivoted) to compress the upper end portion of the stabilizer body 40*p* against the cannula 30 and hold it in position. The bottom of the stabilizer bottom 40*b* can have a flat surface that presses against the skin S. The lock 44 can comprise a clamp configuration which can pivot up and down to lock and unlock or may have other configurations such as a twist lock or other lock configuration.

Figure 17:
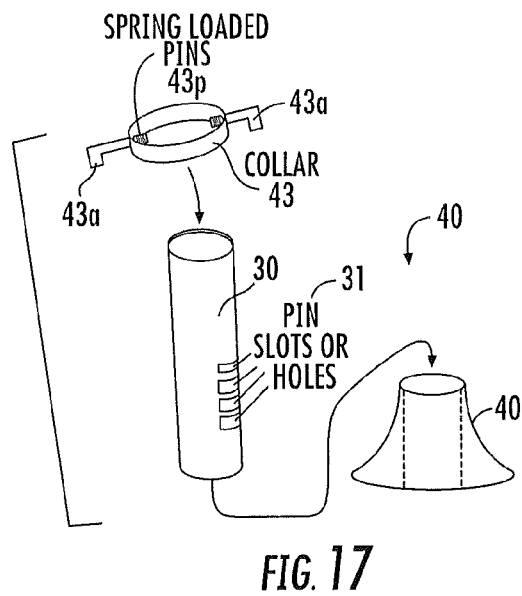
FIG. 17 is an exploded view of another embodiment of a stabilizer device according to embodiments of the present invention.

FIGS. 17, 18A, 18B and 20 illustrate other examples of stabilizers 40 with alternate guide cannula lock configurations. FIG. 17 shows the use of a collar 43 with spring loaded arms or pins 43*a*. The guide cannula 30 can have longitudinally spaced apart pin receiving slots or holes 31 that receive the spring loaded pins 43*p* to lock the collar into a desired location on the guide cannula 30. The pins of the collar 43*a* provide the stop for the stabilizer 40. The tool barrel 10*b* and guide cannula 30 can tilt T during the procedure.

Figures 18A, 18B:
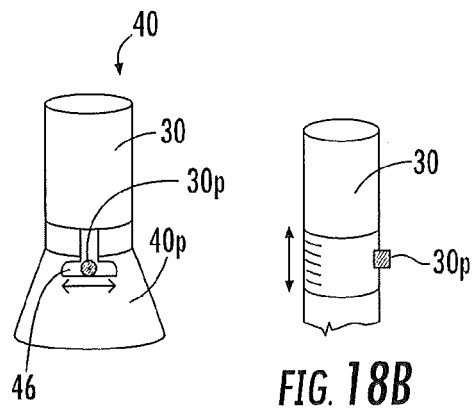
FIG. 18A is a schematic illustration of yet another embodiment of a stabilizer device according to embodiments of the present invention.
FIG. 18B is a partial side view of a guide cannula with depth indicia and locking arm that cooperates with the stabilizer shown in FIG. 18A according to embodiments of the present invention.

FIGS. 18A and 18B illustrate that the stabilizer 40 can have a laterally extending slot 46 that receives at least one pin 30*p* on the guide cannula to lock the guide cannula 30 in a longitudinal direction which can, in some embodiments, define an intrabody depth stop for the distal end 10*d* of the therapy device 10.

FIG. 20 illustrates differently sized/shaped couplers 40H that can interchangeably reside in the stabilizer primary body 40*p* to provide the different stop depths. The couplers 40H can be formed of an elastic and/or resilient material that allows the tilt T for the cannula 30 and tool barrel 10*b*. The couplers 40H can have different configurations, e.g., one or more of different wall thicknesses 40*th*, different tapers and different lengths to provide the desired tool intrabody depth.

FIGS. 19A-19D illustrate alternate exemplary bottoms 40*b* of the stabilizer 40.

The depth stop provided by the stabilizer 40 can be adjustable using the same configured and sized components or different sized/configured components for different patients or treatment sites.

In some embodiments, the order of use of the components where the stabilizer 40 is used can be: insert the guide pin 20, then insert the dilator tube 50. Next, the stabilizer 40 can be placed on the skin S over the guide pin 20 and/or dilator tube 50. The dilator tube 50 can then be removed if it was used. The guide cannula 30 and/or therapy tool 10 can be inserted through the stabilizer 40 with or without the guide pin 20 in place (that is the guide pin 20 can have been previously removed or removed after the cannula 30 and/or tool 10 are inserted through the stabilizer 40). The tool 10 can deliver the therapy to the facet joint J with the pin in position and extending through the pin bore 11 or the therapy to the facet joint can be applied after the pin 20 is withdrawn.

The stop depth provided by the stabilizer 40 and/or stabilizer and guide cannula 30 combination may be adjustable. The clinician can decide an appropriate stop depth for the patient prior to placing one or more of the components in the patient.

Figure 19A:
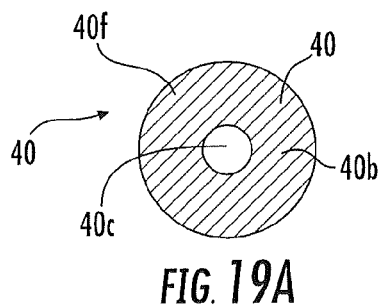
FIGS. 19A-19C are bottom views of exemplary bottom surfaces of a stabilizer device according to embodiments of the present invention.
Figure 19B:
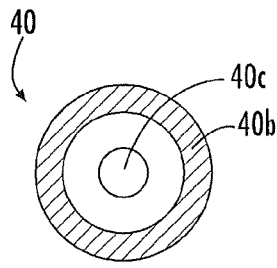
Figure 19C:
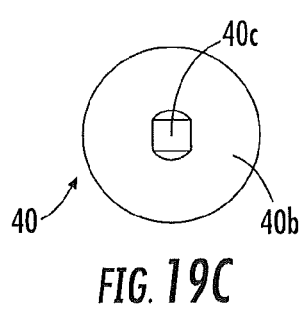
Figure 19D:
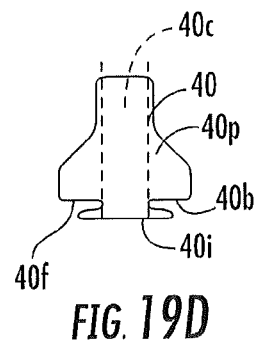
FIG. 19D is a side schematic view of another embodiment of a stabilizer device according to embodiments of the present invention.

The stabilizer 40 can also be placed on the skin S before or after the guide pin 20 is inserted at the treatment joint J. The stabilizer 40 may have a bottom surface 40*b* that can releasably attach to skin of the patient via adhesive or vacuum and the like and define an entry portal for the procedure. The stabilizer 40 may have a distal end portion 40*i* that extends subcutaneously and can engage or lock against skin S from underneath the external primary body 40*b* (FIG. 19D).

FIGS. 21A-21C illustrate examples of spinal therapy treatment systems 100. The systems 100 include the therapy tool 10 and a cautery source 80. The tool 10 can have a pen-form factor such as shown in FIG. 21A or a pistol form factor with a hand portion 10*h* that extends down from the barrel 10*b* as shown in FIGS. 21B and 21C. The motor M that rotates the drive shaft 18 can be onboard or remote from the tool 10. FIG. 21C also shows that the handle 10*h* can be configured to attach to the barrel 10*b* via a pivot attachment 10R to pivot relative to the barrel 10*b* for physician adjustment. The power source for the motor M can be onboard or remote from the tool 10. The power source for the motor M can comprise batteries B and/or a DC or AC power supply.

FIGS. 22A-22C illustrate exemplary therapy systems 100 which can have any suitable form-factor (e.g., the pen shape or the pistol shape or other desired shape). FIG. 22A illustrates the battery B in the handle 10*h* (FIG. 22A) and a cable 101 (e.g., a three wire lead and current plug) that extends from the tool 10 to a connector 10*con*. The connector 10*con* plugs into the cautery generator 80. The battery B can comprise relatively small or light weight batteries such as AA, AAA, pancake shaped batteries or other light-weight batteries. The entire tool 10 with the cable 101 can be sterile and single use disposable.

FIG. 22B illustrates that the battery can be provided as a battery pack 63 that connects via a cable to the tool body 10*b* and/or handle 10*h*. The tool includes a first cable $101_1$ that connects the tool to the battery pack 63 and a second cable $101_2$ that connects the battery pack to the cautery generator 80. The first lead/cable $101_1$ can be a five wire lead to connect to the cautery (3 cautery) and the motor (two for the motor). This configuration may allow a smaller sized tool 10, e.g., smaller handle 10*h*. The battery pack 63 with the battery B can comprise relatively small or light weight batteries such as AA, AAA, pancake shaped batteries or other light-weight batteries. The entire tool 10 with the cables $101_1$, $101_2$ and the battery pack 63 can be sterile and single use disposable.

FIG. 22C illustrates that the tool 10 can connect to a DC (direct current) power supply with a junction housing 66 to connect to the cautery 80. The tool 10 can have a first cable $101_1$ with connector 10*con* that connects to the junction housing 66 and a second cable $101_2$ that connects to the cautery generator 80 via connector 66*c*. The junction housing 66 can also have a power cord 66*p* for connecting to an AC (alternating current) power source. The tool 10, junction 66 and cables $101_1$, $101_2$ can be sterile for medical use. The junction box 66 may be reusable while the tool with first cable $101_1$ and connector 10*con* can be single-use disposable.

FIGS. 23A-23E illustrate exemplary configurations of guide cannulas 30. FIGS. 23C and 23E illustrate a guidewire port 33 on a perimeter thereof (in the wall of the device). FIGS. 23A-23C illustrate circular guide cannulas 30 while FIGS. 23D and E illustrate alternate shapes. FIG. 23A illustrates that the cannula 30 can have a thin wall thickness and may be metal, such as stainless steel. FIGS. 23B-E illustrate thicker wall thicknesses which may be suitable for molded, polymeric cannulas. Laminated or multi-layer guide cannulas 30 with different materials may also be used (FIG. 8).

FIG. 24A illustrates an exemplary spinal facet therapy tool 10 with a barrel 10*b* that rotates to thereby provide the rotating head 15. The tool 10 can be configured to releasably attach different tool barrels 10*b*. The tool 10 can have user inputs 61, shown as buttons for controlling activation/deactivation of the rotation and/or cautery. The tool 10 may have a pistol shape as shown.

FIG. 24A also illustrates that the rotating head 15 can be configured with a fluted configuration 15*f* to inhibit tissue clogging during denuding or tissue scraping. The fluted configuration can have curvilinear longitudinally extending recesses 15*r*.

FIG. 24B illustrates another exemplary spinal facet therapy tool 10. The drive shaft 18 and/or rotatable head 15 can be configured to have a retracted position A inside the tool barrel 10*b* and a deployed (extended) position B for applying the therapy. The tool 10 can have a deploy denude/cautery head user input 61. The input can be provided via touchscreen, trigger, button, slide control, voice command, or any other suitable configuration. The expandable configuration can be used with any form factor tool (e.g., the pen or pistol shape).

FIGS. 27A-27C illustrate an exemplary tool with an expandable cautery/denuding head 15. The tool head 15 can have a first collapsed or unexpanded configuration (FIG. 27B) and an expanded configuration (viewed from an anterior or distal end). This allows a compact delivery profile that can be expanded after delivery to the target region to provide a larger treatment surface area. The expansion can be provided by any number of configurations. FIG. 27A illustrates that the tool can comprises a core that pushes the scraping surface with the electro-cautery region(s) outward. FIG. 24B illustrates a slidably extendable shaft 18 and head 15. The tool barrel 10*b* can also include an outer sheath or housing that can be retracted to expose the cautery/denuding head 15 allowing it to expand (not shown).

FIGS. 25A-25G illustrate that the tool barrel 10*b* can have a fluted distal end 15*f*. As discussed with respect to FIG. 24A above, the fluted end 15*f* can include at least one longitudinally extending recess 15*r* that can inhibit tissue clogging. The flutes 15*f* can be straight (FIG. 25G) or curvilinear (FIGS. 25A, 25B, 25C, 25D, 25E, 25F). The flutes 15*f* can be thin, e.g., between about 1 mm to about 5 mm. The flutes 15*f* can extend longitudinally over a small portion of the length of the shaft and/or barrel 10*b*, such as between about 3 mm to 1 inch, or over substantially a length of the shaft and/or barrel 10*b* sufficient to extend through the working cannula 30, e.g., a length between about 50 mm to about 200 mm, including about 50 mm, about 75 mm, about 100 mm, about 150 mm and about 200 mm. The head lateral dimension can be between about 3-15 mm (if a non-expandable configuration is used) and between about 3-25 mm if an expandable version is used. In some embodiments, a maximal distal head lateral dimension with the flutes 15*f* can be between about 5-15 mm such as about 5 mm, about 6 mm, about 7 mm, about 8 mm, about 9 mm, about 10 mm, about 11 mm, about 12 mm, about 13 mm, about 14 mm, and about 15 mm.

Figure 25A:
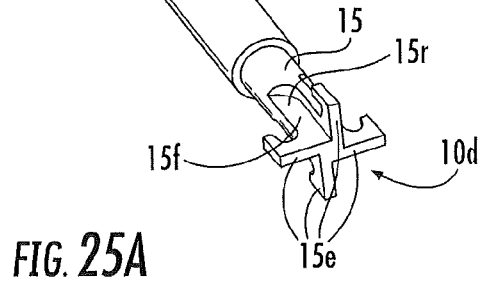
FIGS. 25A-25G are schematic illustrations of electrocautery heads with exemplary cautery and tissue cleansing/scraping surfaces according to embodiments of the present invention.
Figure 25B:
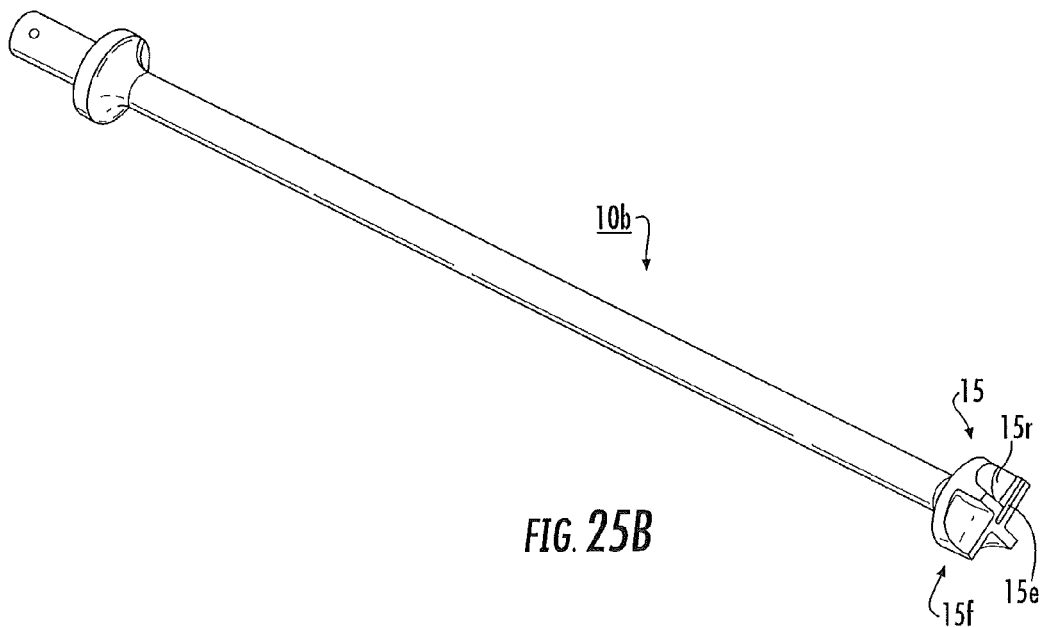
Figure 25C:
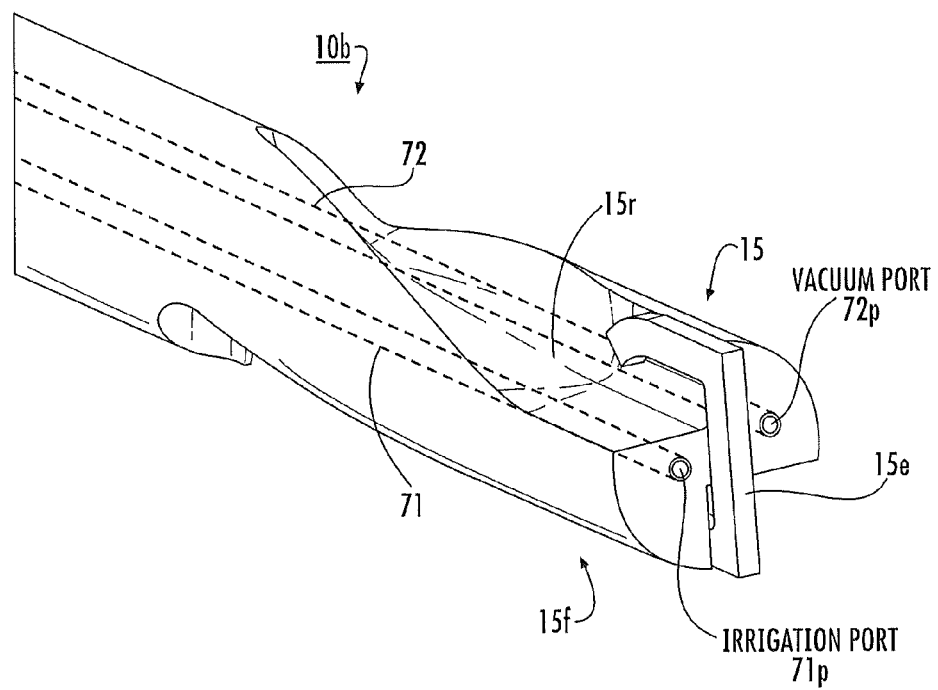
Figure 25D:
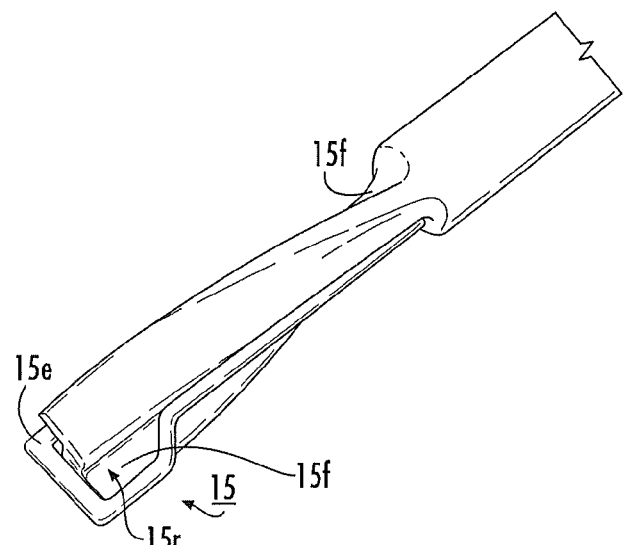
Figure 25E:
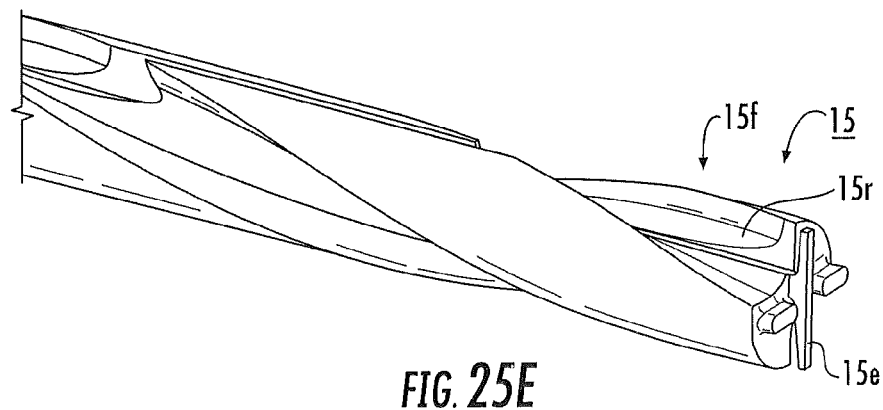
Figure 25F:
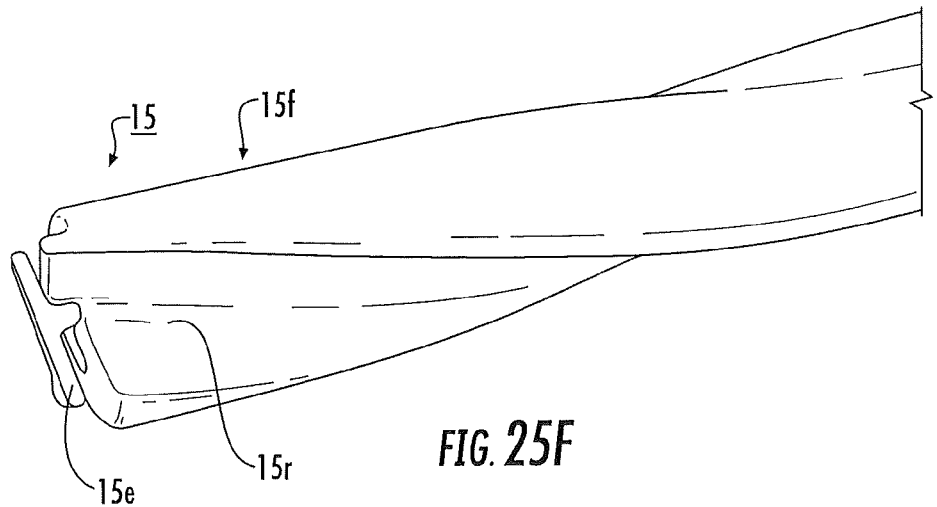
Figure 25G:
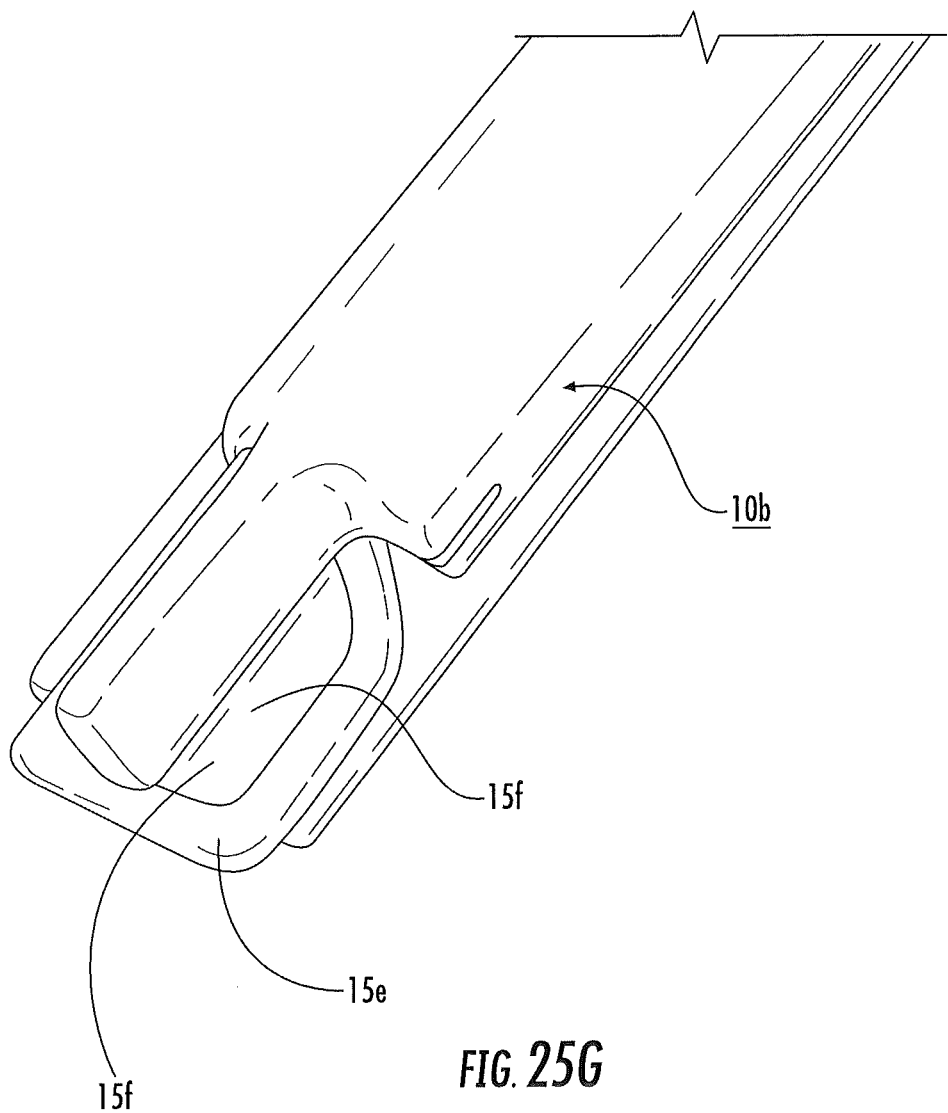

The head 15 can include a single medially located linear electro-cautery segment 15*e* (FIG. 25C, 25E, 25F) or a plurality of electro-cautery surfaces 15*e* interleaved by the grooves or recesses 15*r* (FIGS. 25A, 25B). The head 15 can be a monolithic unitary member with the electrocauthery surface(s) 15*e* and flutes 15*f* (FIGS. 25A, 25B). The entire shaft with the head can be a monolithic conductive member. The head 15 and/or shaft with the head can be a suitable medical grade electrically conductive material such as stainless steel. The head 15 may comprise a discrete electrocautery member 15e that is of a different material than the fluted shaft 15f (FIG. 25C, 25D, 25E, 25F, 25G). That is, as shown, the discrete electrocautery member 15e can reside in or extend from a non-conductive (electrically insulating) shaft or barrel. The discrete electrocautery member 15e can be configured to slidably, longitudinally extend and retract relative to the adjacent non-conductive shaft or barrel or may be statically affixed to same.

It is contemplated that the spinal facet debridement procedure with the combination debrider tool 10 can allow the spinal debridement procedure to be carried out by general surgeons, radiologist, pain medicine, physical medicine, orthopedic and neurosurgeons and/or allow more surgeons to be able to competently carry out the procedure thereby providing more global access to this treatment for patients with longer term pain relief and obviating the need for follow-up treatments upon nerve renervation at the treated spinal facet joint(s).

Embodiments of the invention provide treatment methods that can be carried out at an outpatient clinic and/or as an outpatient procedure at a hospital or surgery center.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention as claimed.

That which is claimed:

1. A set of surgical tools for spinal facet surgical procedures for alleviating spinal pain, comprising:
    a debrider tool having a distal end with a denuding and cauterization head comprising an electrically conductive radially extending straight linear cautery element that extends in a perpendicular direction to and separates non-conductive laterally spaced apart first and second radially extending and linearly straight projections, wherein the debrider tool comprises or is in communication with a motor that drives the denuding and cauterization head to have a maximum rotation speed of between about 10 rpm to about 5000 rpm;
    a dilation tube with a distal end having a tapered end, the dilation tube having a maximum outer diameter that is between about 5 mm to about 15 mm; and
    a cannula sized and configured with a longitudinally extending open primary channel having a width that is between about 5 mm to about 15 mm and that is sized and configured to slidably receive at least the distal end of the debrider tool.

2. The set of surgical tools of claim 1, wherein the dilation tube comprises first and second cooperating tubes, a first inner tube defining the distal end and a second cooperating tube with a tapered forward end that resides upstream of the distal end of the inner tube over the first inner tube, and wherein the second tube is shorter than the first tube and slidably holds the cannula.

3. The set of surgical tools of claim 1, wherein the cannula comprises an open guide pin channel that is laterally spaced apart from the primary channel and extends longitudinally aligned with the primary channel, wherein the guide pin channel has a width that is between about 0.75 mm and about 1.25 mm.

4. The set of surgical tools of claim 1, wherein the debrider tool comprises (a) a drive shaft which merges into the head or (b) an elongate barrel portion that defines an external wall that holds a drive shaft therein, the drive shaft being attached to the head, and wherein the drive shaft and/or elongate barrel portion is sized and configured to be slidably held in the primary channel of the cannula and has a maximal width that is between about 5 mm and about 15 mm.

5. The set of surgical tools of claim 1, further comprising an external stabilizer configured with a bottom surface that is configured to reside against skin of a patient and which is coupled to a tubular segment with an open through channel that releasably holds the cannula in a height-adjustable fixed longitudinal position relative to the external stabilizer.

6. The set of surgical tools of claim 5, wherein the bottom surface of the stabilizer has a width that is between about 2-6 inches.

7. The set of surgical tools of claim 1, wherein the debrider tool has at least one longitudinally extending fluid channel for irrigation and/or suction.

8. The set of surgical tools of claim 1, wherein the debrider tool is configured to have a maximum rotation speed of between about 10 rpm to about 100 rpm.

9. The set of surgical tools of claim 1, wherein the surgical tools are sterile and provided as a kit.

10. The set of surgical tools of claim 1, further comprising batteries held by the debrider tool to power the motor, wherein the motor and batteries are onboard the debrider tool, and wherein the debrider tool comprises a cable with a connector that electrically connects the head to a cautery source.

11. The set of surgical tools of claim 1, wherein the motor is onboard the debrider tool, wherein the surgical tools further comprise a sterile battery pack attached or attachable to the debrider tool by a first sterile cable to power the motor, and wherein the surgical tools include a second sterile cable that connects to the battery pack and a cautery source.

12. The set of surgical tools of claim 1, wherein the motor is held in a junction interface housing, wherein the junction interface housing comprises a direct current (DC) power supply that powers the motor, and wherein the junction interface housing comprises a first cable that connects the junction interface housing DC power supply and a cautery source to the debrider tool, a second cable that connects the junction interface housing to the cautery source, and a third cable that connects the junction interface housing to an alternating current (AC) power source.

13. The set of surgical tools of claim 1, wherein the primary channel of the cannula holds an elongate shaft defining or coupled to the denuding and cauterizing head of the debrider tool, and wherein, in position, a proximal segment of the elongate shaft is above the cannula.

14. The set of surgical tools of claim 1, wherein the projections are defined by a tip of a non-conductive fluted shaft.

15. The set of surgical tools of claim 1, wherein the debrider tool comprises a rotatable shaft that is coupled to or at least partially defines the denuding and cauterization head, wherein the shaft has a fluted configuration with longitudinally extending curvilinear or straight flutes to thereby inhibit tissue aggregation and/or clogging during denuding and/or cauterization.

16. The set of surgical tools of claim 1, wherein the debrider tool comprises a rotatable shaft with a fluted configuration with longitudinally extending curvilinear or straight flutes coupled to or defining at least part of the denuding and cauterization head.

17. The set of surgical tools of claim 1, wherein the debrider tool denuding and cauterization head has a first compact configuration and a second laterally expandable operative configuration that has a perimeter that is larger in at least a lateral dimension relative to the first compact configuration to thereby provide a compact insertion profile and/or a larger treatment surface area.

18. The set of surgical tools of claim 1, wherein the debrider tool comprises a drive shaft that merges into the denuding and cauterization head and that is sized and configured to be slidably held in the cannula.

19. The set of surgical tools of claim 1, wherein the debrider tool comprises a drive shaft that is fluted, and wherein the drive shaft is sized and configured to be slidably held in the primary channel of the cannula and has a maximal width that is between about 5 mm and about 15 mm.

20. The set of surgical tools of claim 1, wherein the cannula comprises an electrically insulating material and externally visible indicia of depth.

21. A spinal facet therapy system to alleviate pain, comprising:
a cautery source;
a spinal facet therapy tool with an elongate shaft having or coupled to a head in communication with the cautery source and configured to automatically rotate at between about 10 rpm to about 5000 rpm during denuding and/or cleansing of respective spinal facet joints to remove an end plate receptor region comprising the synovial capsule of the spinal facet joint thereby treating back pain, wherein the head comprises an electrically conductive radially extending straight linear cautery element that extends in a perpendicular direction to and separates non-conductive laterally spaced apart first and second radially extending and linearly straight projections;
a dilation tube; and
a guide cannula configured to hold the elongate shaft therein while allowing the head to extend out therefrom during active treatment.

22. The system of claim 21, wherein the elongate shaft is a non-conductive fluted shaft.

23. The system of claim 21, wherein the elongate shaft has a fluted configuration with longitudinally extending curvilinear or straight flutes to inhibit tissue aggregation and/or clogging during the denuding and/or cleansing.

24. The system of claim 21, wherein the elongate shaft has a fluted configuration with longitudinally extending curvilinear or straight flutes.

25. The system of claim 21, wherein the head has a first compact configuration and a second laterally expandable operative configuration that has at least a lateral dimension that is larger than the compact configuration to thereby provide a compact insertion profile and/or a larger treatment surface area.

26. The system of claim 21, wherein the elongate shaft has a length with a maximal width that is between about 5 mm and about 15 mm.

27. The system of claim 21, further comprising an external stabilizer having a bottom with a width of between about 2-6 inches and a tubular segment extending above the bottom that releasably holds the guide cannula, wherein the elongate shaft has a non-conductive distal end portion and wherein the elongate shaft is sized and configured to be slidably held in the cannula and has a maximal width that is between about 5 mm and about 15 mm.

28. The system of claim 21, wherein the guide cannula comprises an electrically insulating material and externally visible indicia of depth.

29. A spinal facet surgical tool, comprising:
a debrider tool with a pistol grip holding an elongate non-conductive shaft having a distal end coupled to or having a denuding and cauterization head comprising an electrically conductive radially extending straight linear cautery element that extends in a perpendicular direction to and separates non-conductive laterally spaced apart first and second radially extending and linearly straight projections, wherein the head has a maximal width of between about 5-15 mm, and wherein the shaft comprises longitudinally extending flutes;
a motor in communication with the shaft to drive the denuding and cauterization head; and
a power source in communication with the motor.

30. The tool of claim 29, further comprising an external stabilizer sized and configured to reside against skin of a patient, and a guide cannula releasably held by the external stabilizer that slidably receives the shaft of the debrider tool, wherein the external stabilizer is detached from the debrider tool, wherein the external stabilizer has a base with a width of between about 2-6 inches and a tubular segment extending above the base, wherein the tubular segment releasably holds the guide cannula that slidably receives the shaft of the debrider tool to control an insertion depth of the denuding and cauterization head.

31. The tool of claim 30, wherein the guide cannula comprises an electrically insulating material and externally visible indicia of depth.

32. The tool of claim 29, wherein the denuding and cauterization head has a maximum speed of between about 10 to about 100 rpm.

33. The tool of claim 29, further comprising:
a cautery source;
a cable coupled to the cautery source and the debrider tool, wherein the cautery source supplies power to the linear cautery element.

* * * * *

UNITED STATES PATENT AND TRADEMARK OFFICE
CERTIFICATE OF CORRECTION

PATENT NO.      : 9,883,882 B2
APPLICATION NO. : 14/257490
DATED           : February 6, 2018
INVENTOR(S)     : Haufe et al.

Page 1 of 1

It is certified that error appears in the above-identified patent and that said Letters Patent is hereby corrected as shown below:

In the Specification

Column 19, Line 60: Please correct "30I" to read -- 301 --

Signed and Sealed this
Twenty-ninth Day of May, 2018

Andrei Iancu
*Director of the United States Patent and Trademark Office*